United States Patent
Bhatt et al.

(10) Patent No.: US 11,452,690 B1
(45) Date of Patent: Sep. 27, 2022

(54) ORAL LIQUID COMPOSITIONS COMPRISING AMLODIPINE BESYLATE AND METHODS OF USING THE SAME

(71) Applicant: ECI Pharmaceuticals, LLC, Fort Lauderdale, FL (US)

(72) Inventors: Nirali R. Bhatt, Pompano Beach, FL (US); Alok Kapadia, Lauderhill, FL (US)

(73) Assignee: ECI PHARMACEUTICALS, LLC, Fort Lauderdale, FL (US)

( * ) Notice: Subject to any disclaimer, the term of this patent is extended or adjusted under 35 U.S.C. 154(b) by 0 days.

(21) Appl. No.: 17/345,093

(22) Filed: Jun. 11, 2021

Related U.S. Application Data

(60) Provisional application No. 63/142,116, filed on Jan. 27, 2021.

(51) Int. Cl.
| | |
|---|---|
| *A61K 9/08* | (2006.01) |
| *A61K 9/00* | (2006.01) |
| *A61K 31/4418* | (2006.01) |
| *A61K 47/26* | (2006.01) |
| *A61K 47/14* | (2017.01) |
| *A61K 31/12* | (2006.01) |
| *A61K 47/40* | (2006.01) |

(52) U.S. Cl.
CPC .............. *A61K 9/08* (2013.01); *A61K 9/0053* (2013.01); *A61K 31/12* (2013.01); *A61K 31/4418* (2013.01); *A61K 47/14* (2013.01); *A61K 47/26* (2013.01); *A61K 47/40* (2013.01)

(58) Field of Classification Search
CPC ........ A61K 9/08; A61K 9/0053; A61K 31/12; A61K 31/4418; A61K 47/14; A61K 47/26; A61K 47/40
See application file for complete search history.

(56) References Cited

U.S. PATENT DOCUMENTS

| | | |
|---|---|---|
| 6,046,338 A | 4/2000 | Spargo |
| 6,162,802 A | 12/2000 | Papa et al. |
| 6,245,787 B1 | 6/2001 | Cropp et al. |
| 6,383,471 B1 | 5/2002 | Chen et al. |
| 6,451,339 B2 | 9/2002 | Patel et al. |
| 6,455,574 B1 | 9/2002 | Buch |
| 6,521,647 B2 | 2/2003 | Foster |
| 6,569,463 B2 | 5/2003 | Patel et al. |
| 6,596,874 B1 | 7/2003 | Fischer et al. |
| 6,617,361 B2 | 9/2003 | Eig |
| 6,645,528 B1 | 11/2003 | Straub et al. |
| 6,835,742 B2 | 12/2004 | Mason |
| 6,846,932 B1 | 1/2005 | Joshi et al. |
| 6,923,988 B2 | 8/2005 | Patel et al. |
| 6,932,983 B1 | 8/2005 | Straub et al. |
| 7,070,814 B2 | 7/2006 | Qazi et al. |
| 7,514,105 B2 | 4/2009 | Qazi et al. |
| 7,625,940 B2 | 12/2009 | Solomon |
| 8,101,599 B2 | 1/2012 | Shetty et al. |
| 8,236,782 B2 | 8/2012 | Mosher et al. |
| 8,470,868 B2 | 6/2013 | Waki et al. |
| 8,765,776 B2 | 7/2014 | Kim et al. |
| 9,144,580 B2 | 9/2015 | Sherman et al. |
| 9,579,345 B2 | 2/2017 | Sherman et al. |
| 9,629,920 B2 | 4/2017 | Leighton et al. |
| 9,827,315 B2 | 11/2017 | Patel et al. |
| 10,092,524 B2 | 10/2018 | Macdonald |
| 10,226,423 B1 | 3/2019 | Muni et al. |
| 11,253,474 B1 | 2/2022 | Mandal et al. |
| 2012/0121698 A1 | 5/2012 | Manku et al. |
| 2012/0282335 A1 | 11/2012 | Venkatesh et al. |
| 2016/0128944 A1 | 5/2016 | Chawrai et al. |
| 2018/0042851 A1 | 2/2018 | Guan et al. |
| 2018/0071390 A1 | 3/2018 | Patel et al. |
| 2018/0092908 A1 | 4/2018 | Stockwell et al. |
| 2018/0098978 A1 | 4/2018 | Brauer et al. |
| 2018/0117023 A1 | 5/2018 | Charles et al. |
| 2018/0303811 A1 | 10/2018 | Mandal et al. |
| 2018/0325907 A1 | 11/2018 | Wang et al. |
| 2019/0070184 A1 | 3/2019 | Wang et al. |
| 2019/0091164 A1 | 3/2019 | Horhota et al. |
| 2019/0314279 A1 | 10/2019 | Brauer et al. |

FOREIGN PATENT DOCUMENTS

WO    WO-2012037117 A1 *    3/2012    ........... A61K 31/192

OTHER PUBLICATIONS

NORVASC® (amlodipine besylate) product label, revised Jan. 2019, Pfizer Labs, accessed from http://labeling.pfizer.com/ShowLabeling.aspx?format=PDF&id=562, 15 pages.

\* cited by examiner

*Primary Examiner* — Robert A Wax
*Assistant Examiner* — Quanglong N Truong
(74) *Attorney, Agent, or Firm* — K&L Gates LLP

(57) ABSTRACT

The present disclosure provides oral liquid compositions comprising amlodipine besylate with favorable solubility and stability. Also provided herein are methods of using the oral liquid compositions.

24 Claims, 8 Drawing Sheets

SECTION "A" - "A"

ORAL LIQUID COMPOSITIONS COMPRISING AMLODIPINE BESYLATE AND METHODS OF USING THE SAME

FIELD

The present disclosure relates to oral liquid compositions comprising amlodipine besylate with enhanced stability. The present disclosure also relates to methods of using oral liquid compositions comprising amlodipine besylate for the treatment of disorders including, for example, hypertension, coronary artery disease, and heart failure.

BACKGROUND

Amlodipine is a synthetic dihydropyridine that inhibits the influx of extracellular calcium ions into myocardial and peripheral vascular smooth muscle cells. This inhibition prevents vascular and myocardial contraction, which results in a dilatation of the main coronary and systemic arteries, decreased myocardial contractility, increased blood flow and oxygen delivery to the myocardial tissue, and decreased total peripheral resistance. Amlodipine besylate is a besylate salt of amlodipine and is currently administered as a solid oral dosage form such as, for example, tablets, pills, and capsules.

Oral ingestion is the most convenient and commonly employed route of drug delivery due to ease of administration, high patient compliance, cost effectiveness, reduced sterility constraints, and flexibility in the design of dosage form. However, some patients, specifically pediatric and geriatric patient populations, may dislike or have difficulty swallowing solid oral dosage forms, which can lead to associated disadvantages, such as patient non-compliance. In such situations, oral liquid dosage forms, including solutions, suspensions and emulsions, can be easier to administer and more suitable for use, and can provide greater patient compliance.

Many marketed pharmaceutical products do not have regulatory approval for pediatric use, resulting in "off-label" prescribing by physicians. When a pharmaceutical product does not have a labeled indication for children, manufacturers do not produce strengths and dosage forms appropriate for the pediatric population. Extemporaneously prepared formulations are a sub-optimal option in instances where commercial liquid formulations are not available. At present, liquid dosage forms for amlodipine besylate are prepared by compounding tablets into a suspension. However, developing and compounding of liquid formulations can be challenging for dispensing pharmacists, resulting in a variety of issues, including inaccurate dosing, poor stability, poor taste, adherence problems, and lack of standardizations in extemporaneous compounding. Liquid product compounded by pharmacists may not be made consistently from one pharmacist to another. Further, extemporaneously prepared amlodipine besylate formulations can have a short shelf life.

Accordingly, there is a need for highly stable oral liquid compositions including amlodipine besylate that can address the foregoing problems, and which can provide amlodipine besylate safely, effectively, and consistently to patients who have difficulty swallowing solid dosage forms.

SUMMARY

On non-limiting aspect according to the present disclosure is directed to an oral liquid pharmaceutical composition comprising: about 0.1 to about 1.9 mg/mL amlodipine besylate; about 5 mg/mL to about 90 mg/mL cyclodextrin; about 0.5 mg/mL to about 4 mg/mL paraben; and water. In various non-limiting embodiments, the oral liquid pharmaceutical composition may further include one or more of a sweetener, a flavoring agent, a stabilizer, a coloring agent, and a thickener. In certain non-limiting embodiments, the cyclodextrin comprises β-cyclodextrin. Also, in certain non-limiting embodiments a mole ratio of cyclodextrin to amlodipine besylate in the oral liquid pharmaceutical composition is in a range of about 5:1 to about 75:1. In certain non-limiting embodiments, the oral liquid pharmaceutical composition according to the present disclosure The oral liquid composition of claim 21, wherein the oral liquid pharmaceutical composition further comprises about 0.02 mg/mL to about 0.12 mg/mL curcumin.

An addition non-limiting aspect according to the present disclosure is directed to an oral liquid pharmaceutical composition comprising: about 0.8 to about 1.2 mg/mL amlodipine besylate; about 10 mg/mL to about 60 mg/mL cyclodextrin; about 1.5 mg/mL to about 2.5 mg/mL paraben; and water. In certain non-limiting embodiments of the oral liquid pharmaceutical composition the cyclodextrin comprises β-cyclodextrin. In various non-limiting embodiments of the oral liquid pharmaceutical composition, a mole ratio of cyclodextrin to amlodipine besylate is about 5:1 to about 75:1.

The oral liquid pharmaceutical composition according to the present disclosure exhibits favorable stability characteristic. In certain non-limiting embodiments of the oral liquid pharmaceutical composition according to the present disclosure, a volume of the composition retains at least 90% of an initial concentration of amlodipine besylate after the volume has been stored in a sealed container for three months at 23° C. to 27° C. and 55% to 65% relative humidity. In certain non-limiting embodiments of the oral liquid pharmaceutical composition according to the present disclosure, a volume of the composition retains at least 90% of an initial concentration of amlodipine besylate after the volume has been stored in a sealed container for six months at 23° C. to 27° C. and 55% to 65% relative humidity. In certain non-limiting embodiments of the oral liquid pharmaceutical composition according to the present disclosure, a volume of the composition retains at least 95% of an initial concentration of amlodipine besylate after the volume has been stored in a sealed container for three months at 23° C. to 27° C. and 55% to 65% relative humidity. In certain non-limiting embodiments of the oral liquid pharmaceutical composition according to the present disclosure, a volume of the composition retains at least 95% of an initial concentration of amlodipine besylate after the volume has been stored in a sealed container for six months at 23° C. to 27° C. and 55% to 65% relative humidity.

In certain non-limiting embodiments of the oral liquid pharmaceutical composition according to the present disclosure, a volume of the composition retains at least 90% of an initial concentration of amlodipine besylate after the volume has been stored in a sealed container for three months at 2° C. to 8° C. In certain non-limiting embodiments of the oral liquid pharmaceutical composition according to the present disclosure, a volume of the composition retains at least 90% of an initial concentration of amlodipine besylate after the volume has been stored in a sealed container for six months at 2° C. to 8° C. In certain non-limiting embodiments of the oral liquid pharmaceutical composition according to the present disclosure, a volume of the composition retains at least 95% of an initial concentration of amlodipine besylate after the volume has been stored in a sealed container for three months at 2° C. to 8° C. In certain non-limiting embodiments of the oral liquid pharmaceutical composition according to the present disclosure, a volume of the composition retains at least 95% of an initial concentration of amlodipine besylate after the volume has been stored in a sealed container for six months at 2° C. to 8° C.

In certain non-limiting embodiments of the oral liquid pharmaceutical composition according to the present disclosure, a volume of the composition retains at least 90% of an initial concentration of amlodipine besylate after the volume has been stored in a sealed container for three months at 28° C. to 32° C. and 60% to 70% relative humidity. In certain non-limiting embodiments of the oral liquid pharmaceutical composition according to the present disclosure, a volume of the composition retains at least 90% of an initial concentration of amlodipine besylate after the volume has been stored in a sealed container for six months at 28° C. to 32° C. and 60% to 70% relative humidity. In certain non-limiting embodiments of the oral liquid pharmaceutical composition according to the present disclosure, a volume of the composition retains at least 95% of an initial concentration of amlodipine besylate after the volume has been stored in a sealed container for three months at 28° C. to 32° C. and 60% to 70% relative humidity. In certain non-limiting embodiments of the oral liquid pharmaceutical composition according to the present disclosure, a volume of the composition retains at least 95% of an initial concentration of amlodipine besylate after the volume has been stored in a sealed container for six months at 28° C. to 32° C. and 60% to 70% relative humidity.

In certain non-limiting embodiments of the oral liquid pharmaceutical composition according to the present disclosure, a volume of the composition retains at least 90% of an initial concentration of amlodipine besylate after the volume has been stored in a sealed container for one month at 38° C. to 42° C. and not greater than 25% relative humidity. In certain non-limiting embodiments of the oral liquid pharmaceutical composition according to the present disclosure, a volume of the composition retains at least 90% of an initial concentration of amlodipine besylate after the volume has been stored in a sealed container for three months at 38° C. to 42° C. and not greater than 25% relative humidity. In certain non-limiting embodiments of the oral liquid pharmaceutical composition according to the present disclosure, a volume of the composition retains at least 95% of an initial concentration of amlodipine besylate after the volume has been stored in a sealed container for three months at 38° C. to 42° C. and not greater than 25% relative humidity.

A further aspect of the present disclosure is directed to a method of treating a condition selected from hypertension, heart failure, and coronary artery disease. The method comprises administering to a subject in need thereof a therapeutically effective amount of an oral liquid pharmaceutical composition according to the present disclosure. In certain embodiments, the oral liquid pharmaceutical composition comprises: about 0.1 to about 1.9 mg/mL amlodipine besylate; about 5 mg/mL to about 90 mg/mL cyclodextrin; about 0.5 mg/mL to about 4 mg/mL paraben; and water.

The foregoing summary is illustrative only and is not intended to be in any way limiting. In addition to the illustrative examples and features described herein, further aspects, examples, objects and features of the disclosure will become fully apparent from the drawings, the detailed description, and the claims.

BRIEF DESCRIPTION OF THE DRAWINGS

Various features and characteristics of non-limiting and non-exhaustive embodiments disclosed and described in this specification may be better understood by reference to the accompanying figures, in which:

FIGS. 2A-2C are views of a 4 ounce container used to contain an oral liquid composition, as described herein, wherein FIG. 2A is an isometric view of the container, FIG. 2B is an elevational view of the container, and FIG. 2C is a plan bottom view of the container.

FIGS. 3A-3D are views of a ribbed, threaded container closure that can be used in conjunction with the container shown in FIGS. 2A-2C, wherein FIG. 3A is an isometric view of the container closure, FIG. 3B is an exterior top view of the container closure, FIG. 3C is an exterior elevational view of the container closure, and FIG. 3D is a sectional view of the container closure taken along line A-A in FIG. 3B.

Figure 1:
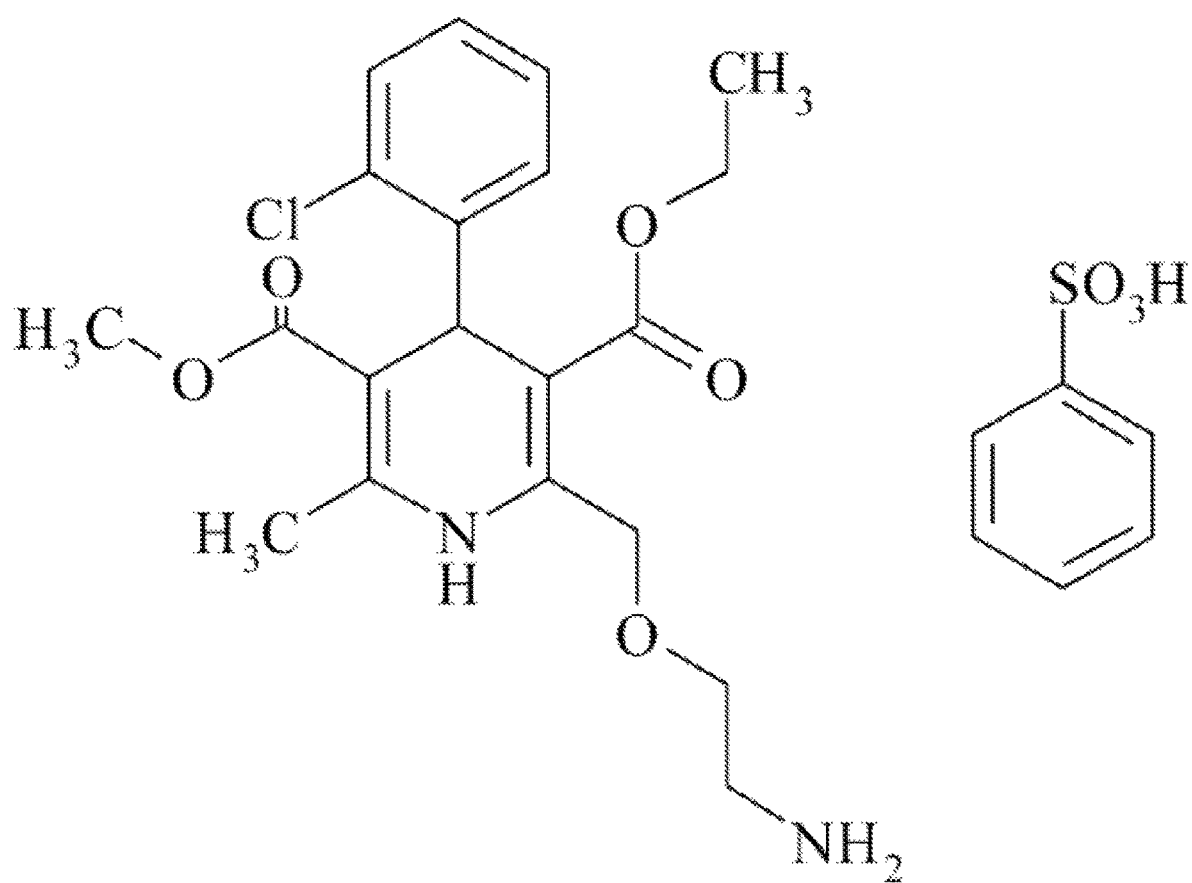
FIG. 1 illustrates the chemical structure of amlodipine besylate.

The reader will appreciate the foregoing details, as well as others, upon considering the following detailed description of various non-limiting and non-exhaustive embodiments according to the present disclosure.

DETAILED DESCRIPTION

Various embodiments are described and illustrated in this specification to provide an overall understanding of the disclosed compositions and methods. It is understood that the various embodiments described and illustrated in this specification are non-limiting and non-exhaustive. Thus, the present invention is not limited by the description of the various non-limiting and non-exhaustive embodiments disclosed in this specification. Rather, the invention is defined solely by the claims. Certain features and characteristics illustrated and/or described in connection with various embodiments may be combined with the features and characteristics of other embodiments. Such modifications and variations are intended to be included within the scope of this specification. As such, the claims may be amended to recite any features or characteristics expressly or inherently described in, or otherwise expressly or inherently supported by, this specification. Further, Applicant reserves the right to amend the claims to affirmatively disclaim features or characteristics that may be found present in the prior art. The various embodiments disclosed and described in this specification can comprise, consist of, or consist essentially of the features and characteristics as variously described herein.

Any numerical ranges recited in this specification are intended to include all sub-ranges of the same numerical precision subsumed within the recited range. For example, a range of "1.0 to 10.0" is intended to include all sub-ranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited in this specification is intended to include all lower numerical limitations subsumed therein and any minimum numerical limitation recited in this specification is intended to include all higher numerical limitations subsumed therein. Applicant reserves the right to amend this specification, including the claims, to recite expressly any sub-range subsumed within the ranges expressly recited herein.

Any patent, publication, or other disclosure material that is said to be incorporated herein, in whole or in part, by reference herein is incorporated herein only to the extent that the incorporated material does not conflict with existing definitions, statements, or other disclosure material set forth in this disclosure. As such, and to the extent necessary, the disclosure as set forth herein supersedes any conflicting material incorporated herein by reference. Any material, or portion thereof, that is said to be incorporated by reference herein, but which conflicts with existing definitions, statements, or other disclosure material set forth herein is only incorporated to the extent that no conflict arises between that incorporated material and the existing disclosure material.

Provided herein are stable oral liquid compositions comprising amlodipine besylate. As used herein, "amlodipine besylate" refers to 3-ethyl-5-methyl-2-[(2-aminoethoxy) methyl]-4-(2-chlorophenyl)-6-methyl-1,4-dihydropyridine-3,5-dicarboxylate, which has the empirical formula $C_{26}H_{31}ClN_2O_8S$ and the chemical structure shown in FIG. 1. Amlodipine besylate suitable for pharmaceutical applications can be purchased from various commercial sources.

The oral liquid compositions comprising amlodipine besylate according to the present disclosure can be useful in treatment of conditions including, for example, hypertension, coronary artery disease, and heart failure. The compositions can provide advantages over conventional solid dosage form administration of amlodipine besylate including, for example, enhanced stability, ease of administration, increased patient compliance, and accurate/precise delivery of amlodipine besylate to the patient. The terms "subject" and "patient" are used interchangeably herein, and it is intended that both refer to a recipient on whom a method is conducted according to the present disclosure or another method, as the case may be.

The oral liquid compositions comprising amlodipine besylate according to the present disclosure further comprise one or more cyclodextrins, as further described herein. As known to those having ordinary skill, cyclodextrins are a family of cyclic oligosaccharides, including of a macrocyclic ring of six to eight glucose subunits joined by α-1,4 glycosidic bonds, creating a generally cone-shaped molecule including a hydrophilic exterior and a hydrophobic interior. Cyclodextrins conventionally may be produced from starch by enzymatic conversion. Compounds within the family of cyclodextrins include α (alpha)-cyclodextrin (including six glucose subunits), β (beta)-cyclodextrin (seven glucose subunits), and γ (gamma)-cyclodextrin (eight glucose subunits). These core structures can be substituted with various groups and moieties to create particular cyclodextrin molecules. For example, the cyclodextrin structure's hydroxyl groups can be manipulated by chemical modification, with O-methylation and acetylation being typical conversions.

The oral liquid compositions according to the present disclosure may further comprise curcumin. As is known in the art, curcumin is a diarylheptanoid, which include two aromatic rings joined by a seven carbon chain including various substituents. Curcumin is a tautomeric compound existing in enolic form in organic solvents and in keto form in water. In certain non-limiting embodiments, the curcumin addition during production of the compositions according to the present disclosure may be by addition of a curcumin solution to the ingredients such as, for example, a solution of 0.03% w/w curcumin and 99.97% w/w propylene glycol. It is believed that curcumin functions as a stabilizer in the oral compositions according to the present disclosure.

The oral liquid compositions according to the present disclosure can optionally further comprise a preservative, for example, one or more parabens. The oral liquid compositions may optionally include other excipients, as discussed herein.

Oral liquid compositions according to the present disclosure may comprise amlodipine besylate, cyclodextrin, and curcumin in concentrations and concentration ratios providing an unexpectedly high solubility of the amlodipine besylate in the compositions, as well as unexpectedly high stability. As discussed herein, the present inventors discovered that embodiments of oral liquid compositions comprising amlodipine besylate, cyclodextrin, and curcumin surprisingly and unexpectedly provide highly advantageous stability of amlodipine besylate. For example, the present inventors unexpectedly observed that certain embodiments of oral liquid compositions according to the present disclosure comprising amlodipine besylate, cyclodextrin, and curcumin were stable (i.e. at least 90% of an initial amount of the amlodipine besylate remained in the composition) after being stored for any of 3 months under accelerated conditions (40° C.±° C. and 75%±5% relative humidity (RH)), 6 months under intermediate conditions (30° C.±2° C. and 65%±5% RH), 6 months under controlled room temperature conditions (25° C.±2° C. and 60%±5% RH), and 6 months under refrigerated conditions (5° C.±3° C.).

Further discussion regarding the ingredients that are or may be present in the oral liquid compositions according to the present disclosure follows.

Amlodipine Besylate

Amlodipine besylate may be present in oral liquid compositions according to the present disclosure in a concentration range of about 0.8 mg/mL to about 1.2 mg/mL, based on the volume of the oral liquid composition, or in any concentration or within any concentration range subsumed therein. Various non-limiting embodiments of oral liquid compositions according to the present disclosure may include amlodipine besylate in a concentration range from about 0.1 mg/mL to about 1.9 mg/mL, about 0.2 mg/mL to about 1.8 mg/mL, about 0.3 mg/mL to about 1.7 mg/mL, about 0.4 mg/mL to about 1.6 mg/mL, about 0.5 mg/mL to about 1.5 mg/mL, about 0.6 mg/mL to about 1.4 mg/mL, about 0.7 mg/mL to about 1.3 mg/mL, about 0.8 mg/mL to about 1.2 mg/mL, about 0.9 mg/mL to about 1.1 mg/mL, about 0.5 mg/mL to about 1.1 mg/mL, about 0.6 mg/mL to about 1.1 mg/mL, about 0.7 mg/mL to about 1.1 mg/mL, about 0.8 mg/mL to about 1.1 mg/mL, about 0.5 mg/mL to about 1.2 mg/mL, about 0.6 mg/mL to about 1.2 mg/mL, about 0.7 mg/mL to about 1.2 mg/mL, about 0.8 mg/mL to about 1.2 mg/mL, about 0.5 mg/mL to about 1.3 mg/mL, about 0.6 mg/mL to about 1.3 mg/mL, about 0.7 mg/mL to about 1.3 mg/mL, or about 0.8 mg/mL to about 1.3 mg/mL, based on the volume of the oral liquid composition. In certain non-limiting embodiments of oral liquid compositions according to the present disclosure, amlodipine besylate can be present in a concentration of about 0.8 mg/mL, about 0.9 mg/mL, about 1.0 mg/mL, about 1.1 mg/mL, about 1.2 mg/mL, or about 1.3 mg/mL, based on the volume of the oral liquid composition.

Cyclodextrin

Cyclodextrin included in oral liquid compositions according to the present disclosure can be one or more α-cyclodextrin compounds, one or more β-cyclodextrin compounds, and/or one or more γ-cyclodextrin compounds. In certain non-limiting embodiments according to the present disclosure, the liquid oral compositions comprise β-cyclodextrin.

In various non-limiting embodiments according to the present disclosure, the liquid oral compositions comprise hydroxypropyl β-cyclodextrin. Hydroxypropyl-β-cyclodextrin (HP-β-CD) is a cyclic oligosaccharide containing seven D-(+)-glucopyranose units. The circular arrangement of its glucose units produces a torus-shaped ring configuration in which the $CH_2$ groups and ether linkages of the molecule face the hollow interior, resulting in a nonpolar, hydrophobic cavity and a polar, hydrophilic exterior. Without wishing to be bound to any theory, nonpolar aromatic portions of amlodipine besylate interact with the nonpolar interior of the HP-β-CD molecule in compositions according to the present disclosure, isolating the aromatic portion of the molecule from polar solvent (e.g., water), and thereby increasing solubility of the amlodipine besylate in the solvent.

Cyclodextrin can be present in the oral liquid compositions according to the present disclosure in a concentration range of about 5 mg/mL to about 100 mg/mL, based on the volume of the oral liquid composition, or in any concentration or within any concentration range subsumed therein. In certain non-limiting embodiments of the oral liquid compositions according to the present disclosure, cyclodextrin is present in a concentration from about 5 mg/mL to about 90 mg/mL, about 10 mg/mL to about 90 mg/mL about 15 mg/mL to about 85 mg/mL, about 20 mg/mL to about 80 mg/mL, about 25 mg/mL to about 75 mg/mL, about 30 mg/mL to about 70 mg/mL, about 35 mg/mL to about 65 mg/mL, about 40 mg/mL to about 60 mg/mL, or about 45 mg/mL to about 55 mg/mL, based on the volume of the oral liquid composition. In various non-limiting embodiments, the oral liquid compositions according to the present disclosure include cyclodextrin in a concentration of about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 45 mg/mL, about 46 mg/mL, about 47 mg/mL, about 48 mg/mL, about 49 mg/mL, about 50 mg/mL, about 51 mg/mL, about 52 mg/mL, about 53 mg/mL, about 54 mg/mL, or about 55 mg/mL, based on the volume of the oral liquid composition.

If present in the oral liquid compositions according to the present disclosure, β-cyclodextrin can be present in a concentration range of about 5 mg/mL to about 100 mg/mL, based on volume of the oral liquid composition, or in any concentration or within any concentration range subsumed therein. In various non-limiting embodiments of the oral liquid compositions according to the present disclosure, β-cyclodextrin is present in a concentration of about 5 mg/mL to about 90 mg/mL, about 10 mg/mL to about 90 mg/mL, about 15 mg/mL to about 85 mg/mL, about 20 mg/mL to about 80 mg/mL, about 25 mg/mL to about 75 mg/mL, about 30 mg/mL to about 70 mg/mL, about 35 mg/mL to about 65 mg/mL, about 40 mg/mL to about 60 mg/mL, or about 45 mg/mL to about 55 mg/mL, based on the volume of the oral liquid composition. In various non-limiting embodiments, β-cyclodextrin can be present in the oral liquid compositions according to the present disclosure in a concentration of about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 45 mg/mL, about 46 mg/mL, about 47 mg/mL, about 48 mg/mL, about 49 mg/mL, about 50 mg/mL, about 51 mg/mL, about 52 mg/mL, about 53 mg/mL, about 54 mg/mL, or about 55 mg/mL, based on the volume of the oral liquid composition.

If present in the oral liquid compositions according to the present disclosure, HP-β-cyclodextrin can be present in a concentration range of about 5 mg/mL to about 100 mg/mL of the oral liquid composition, based on volume of the oral liquid composition, or in any concentration or within any concentration range subsumed therein. In various non-limiting embodiments of the oral liquid compositions according to the present disclosure, The HP-β-cyclodextrin is present in a concentration range of about 10 mg/mL to about 90 mg/mL, about 15 mg/mL to about 85 mg/mL, about 20 mg/mL to about 80 mg/mL, about 25 mg/mL to about 75 mg/mL, about 30 mg/mL to about 70 mg/mL, about 35 mg/mL to about 65 mg/mL, about 40 mg/mL to about 60 mg/mL, or about 45 mg/mL to about 55 mg/mL, based on the volume of the oral liquid composition. In certain non-limiting embodiments of oral liquid compositions according to the present disclosure, HP-β-cyclodextrin is present in a concentration of about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 45 mg/mL, about 46 mg/mL, about 47 mg/mL, about 48 mg/mL, about 49 mg/mL, about 50 mg/mL, about 51 mg/mL, about 52 mg/mL, about 53 mg/mL, about 54 mg/mL, or about 55 mg/mL, based on the volume of the oral liquid composition.

Curcumin

Curcumin may be present in various embodiments of the oral liquid compositions according to the present disclosure in a concentration range of about 0.02 mg/mL to about 0.12 mg/mL of the oral liquid composition, based on volume of the oral liquid composition, or in any concentration or within any concentration range subsumed therein. In various non-limiting embodiments of an oral liquid compositions according to the present disclosure, curcumin is present in a concentration range of about 0.03 mg/mL to about 0.12 mg/mL, about 0.03 mg/mL to about 0.11 mg/mL, about 0.03 mg/mL to about 0.10 mg/mL, about 0.03 mg/mL to about 0.09 mg/mL, about 0.03 mg/mL to about 0.08 mg/mL, about 0.03 mg/mL to about 0.07 mg/mL, about 0.03 mg/mL to about 0.06 mg/mL, about 0.04 mg/mL to about 0.12 mg/mL, about 0.04 mg/mL to about 0.11 mg/mL, about 0.04 mg/mL to about 0.10 mg/mL, about 0.04 mg/mL to about 0.09 mg/mL, about 0.04 mg/mL to about 0.08 mg/mL, about 0.04 mg/mL to about 0.07 mg/mL, about 0.04 mg/mL to about 0.06 mg/mL, about 0.05 mg/mL to about 0.12 mg/mL, about 0.05 mg/mL to about 0.11 mg/mL, about 0.05 mg/mL to about 0.10 mg/mL, about 0.05 mg/mL to about 0.09 mg/mL, about 0.05 mg/mL to about 0.08 mg/mL, about 0.05 mg/mL to about 0.07 mg/mL, about 0.06 mg/mL to about 0.12 mg/mL, about 0.06 mg/mL to about 0.11 mg/mL, about 0.06 mg/mL to about 0.10 mg/mL, about 0.06 mg/mL to about 0.09 mg/mL, about 0.06 mg/mL to about 0.08 mg/mL, or about 0.06 mg/mL to about 0.07 mg/mL, based on the volume of the oral liquid composition. In certain non-limiting embodiments of oral liquid compositions according to the present disclosure, curcumin is present in a concentration of about 0.02 mg/mL, about 0.03 mg/mL, about 0.04 mg/mL, about 0.05 mg/mL, about 0.06 mg/mL, about 0.07 mg/mL, about 0.08 mg/mL, about 0.09 mg/m/L, about 0.10 mg/mL, about 0.11 mg/mL, or about 0.12 mg/mL, based on the volume of the oral liquid composition. Without wishing to be bound by any theory, it is believed that improved stability of various embodiments of oral liquid compositions disclosed herein is at least partially attributable to the presence of curcumin in the compositions.

Paraben

Paraben can be present in various non-limiting embodiments of oral liquid compositions according to the present disclosure. If present, paraben can be present in a concentration sufficient to prevent or inhibit the growth of bacteria, mold, or other undesirable microbes. If present in the oral liquid compositions, paraben can be or can include one or more of methylparaben, ethylparaben, propylparaben, and butylparaben, and/or any other paraben compound providing anti-microbial activity.

If present in the oral liquid compositions according to the present disclosure, paraben can be present in a concentration range of from about 0.5 mg/mL to about 4 mg/mL of the oral liquid composition, based on the volume of the oral liquid composition, or in any concentration or within any concentration range subsumed therein. In various non-limiting embodiments of oral liquid compositions according to the present disclosure, paraben can be present in a concentration range of about 0.6 mg/mL to about 3.9 mg/mL, about 0.7 mg/mL to about 3.8 mg/mL, about 0.8 mg/mL to about 3.7 mg/mL, about 0.9 mg/mL to about 3.6, about 1.1 mg/mL to about 2.9 mg/mL, about 1.2 mg/mL to about 2.8 mg/mL, about 1.3 mg/mL to about 2.7 mg/mL, about 1.4 mg/mL to about 2.6 mg/mL, or about 1.5 mg/mL to about 2.5 mg/mL, based on the volume of the oral liquid composition.

Various non-limiting embodiments of the oral liquid compositions according to the present disclosure include methylparaben. Non-limiting embodiments of the present oral liquid compositions may include methylparaben in a concentration range of about 0.5 mg/mL to about 4 mg/mL, or about 1.8 mg/mL to about 2.2 mg/mL, based on the volume of the oral liquid composition, or in any concentration or within any concentration range subsumed therein. In certain non-limiting embodiments of the oral liquid compositions according to the present disclosure, methylparaben can be present in a concentration range of about 0.6 mg/mL to about 3.9 mg/mL, about 0.7 mg/mL to about 3.8 mg/mL, about 0.8 mg/mL to about 3.7 mg/mL, about 0.9 mg/mL to about 3.6, about 1.1 mg/mL to about 2.9 mg/mL, about 1.2 mg/mL to about 2.8 mg/mL, about 1.3 mg/mL to about 2.7 mg/mL, about 1.4 mg/mL to about 2.6 mg/mL, or about 1.5 mg/mL to about 2.5 mg/mL, based on the volume of the oral liquid composition. In various non-limiting embodiments of the oral liquid compositions according to the present disclosure, methylparaben can be present in a concentration of about 1.8 mg/mL, about 1.9 mg/mL, about 2.0 mg/mL, about 2.1 mg/mL, or about 2.2 mg/mL, based on the volume of the oral liquid composition.

Mole Ratios

In various non-limiting embodiments of the oral liquid compositions according to the present disclosure, a mole ratio of cyclodextrin to amlodipine besylate is in a range of about 5:1 to about 75:1, or is any mole ratio or within any mole ratio range subsumed therein. In certain non-limiting embodiments of the oral liquid compositions the mole ratio of cyclodextrin to amlodipine besylate is about 10:1, about 15:1, about 20:1, about 25:1, about 30:1 about 35:1, about 40:1, about 45:1, about 50:1, about 55:1, about 60:1, about 65:1, about 70:1, or about 75:1.

In various non-limiting embodiments of the oral liquid compositions according to the present disclosure, a mole ratio of β-cyclodextrin to amlodipine besylate is in a range of about 5:1 to about 75:1, or is any mole ratio or within any mole ratio subsumed therein. In certain non-limiting embodiments of the oral liquid compositions the mole ratio of β-cyclodextrin to amlodipine besylate is about 10:1, about 15:1, about 20:1, about 25:1, about 30:1 about 35:1, about 40:1, about 45:1, about 50:1, about 55:1, about 60:1, about 65:1, about 70:1, or about 75:1.

In various non-limiting embodiments of the oral liquid compositions according to the present disclosure, a mole ratio of HP-β-cyclodextrin to amlodipine besylate is in a range of about 5:1 to about 75:1, or is any mole ratio or within any mole ratio subsumed therein. In certain non-limiting embodiments of the oral liquid compositions the mole ratio of HP-β-cyclodextrin to amlodipine besylate is about 10:1, about 15:1, about 20:1, about 25:1, about 30:1 about 35:1, about 40:1, about 45:1, about 50:1, about 55:1, about 60:1, about 65:1, about 70:1, or about 75:1.

In various non-limiting embodiments of the oral liquid compositions according to the present disclosure, a mole ratio of curcumin to amlodipine besylate is in a range of about 150:1 to about 250:1, or is any mole ratio or within any mole ratio range subsumed therein. In certain non-limiting embodiments of the oral liquid compositions the mole ratio of curcumin to amlodipine besylate is about 150:1, about 155:1, about 160:1, about 165:1, about 170:1, about 175:1, about 180:1, about 185:1, about 190:1, about 195:1, about 200:1, about 205:1, about 210:1, about 215:1, about 220:1, about 225:1, about 230:1, about 235:1, about 240:1, about 245:1, or about 250:1.

In various non-limiting embodiments of the oral liquid compositions according to the present disclosure that include paraben, a mole ratio of paraben to amlodipine besylate is in a range of about 1:1 to about 2:1. In certain non-limiting embodiments of the oral liquid compositions, the mole ratio of paraben to amlodipine besylate is about 1:1, about 1.1:1, about 1.2:1, about 1.3:1, about 1.4:1, about 1.5:1, about 1.6:1, about 1.7:1, about 1.8:1, about 1.9:1, about 2:1, about 2.1:1, about 2.1.1:1, or about 2.1:1.1.

Additional Excipients

The oral liquid compositions according to the present disclosure can optionally comprise one or more additional excipients, including but not limited to, sweeteners, flavoring agents, stabilizers, coloring agents, thickeners and the like. Additional excipients can be selected based on function and compatibility with the oral liquid compositions disclosed herein, and various possible excipients may be found, for example, in Remington: The Science and Practice of Pharmacy, Nineteenth Ed. (Easton, Pa.: Mack Publishing Company, 1995); Hoover, John E., Remington's Pharmaceutical Sciences, (Easton, Pa.: Mack Publishing Company, 1975); Liberman, H. A. and Lachman, L., Eds., Pharmaceutical Dosage Forms (New York, N.Y.: Marcel Decker, 1980); and Pharmaceutical Dosage Forms and Drug Delivery Systems, Seventh Ed. (Lippincott Williams & Wilkins, 1999), Kibbe, Arthur H., "Handbook of Pharmaceutical Excipients" (3rd ed.) (2000), all of which are herein incorporated by reference in their entirety.

One or more sweeteners or sweetening agents can be included in the liquid compositions according to the present disclosure and can include any compound or compounds that provide a sweet taste, including, for example, natural and synthetic sugars, natural and artificial sweeteners, natural extracts, and any suitable compound or material that initiates a sweet sensation in a subject. For example, solid, powder sweeteners can be included as ingredients in the oral liquid compositions disclosed herein. Alternatively or additionally, sweeteners in liquid form, also referred to as syrups, can be included in the oral liquid compositions disclosed herein.

Suitable sweeteners for inclusion in non-limiting embodiments of the oral liquid compositions according to the present disclosure can include, but are not limited to, glucose, fructose, sucrose, xylitol, tagatose, sucralose, maltitol, isomaltulose, ISOMALT™ (hydrogenated isomaltulose), lactitol, sorbitol, mannitol, erythritol, trehalose, maltodextrin, polydextrose, and the like. Other sweeteners that may be included in the oral liquid compositions herein include, for example, glycerin, inulin, erythritol, maltol, acesulfame and salts thereof (e.g., acesulfame potassium), alitame, aspartame, neotame, sodium cyclamate, saccharin and salts thereof (e.g., saccharin sodium or saccharin calcium), neohesperidin dihydrochalcone, stevioside, thaumatin, and the like. Sweeteners can be used in the form of crude or refined products, such as, for example, hydrogenated starch hydrolysates, maltitol syrup, high fructose corn syrup, etc., and as branded products, e.g., SWEET AM™ liquid (Product Code 918.003—propylene glycol, ethyl alcohol, and proprietary artificial flavor combination, Flavors of North America), SWEET AM™ powder (Product Code 918.005—maltodextrin, sorbitol, and fructose combination, and Product Code 918.010—water, propylene glycol, sorbitol, fructose, and proprietary natural and artificial flavor combination, Flavors of North America), PROSWEET™ sweetener (1-10% proprietary plant/vegetable extract and 90-99% dextrose combination, Virginia Dare), MALTISWEET™ sweetener (maltitol solution, Ingredion), SORBO™ sweetener (sorbitol and sorbitol/xylitol solution, SPI Polyols), INVERTOSE™ sweetener (high fructose corn syrup, Ingredion), and ORA-SWEET™ sugar-free flavored syrup (Paddock Laboratories, Inc.). Sweeteners can be used singly or in combinations of two or more. Suitable concentrations of the possible sweeteners can be selected based on published information, manufacturers' data sheets, and/or by routine testing.

In certain non-limiting oral liquid compositions according to the present disclosure, the compositions comprise sucralose as a sweetener. Sucralose can be present in the present oral liquid compositions in a concentration range of about 0.1 mg/mL to about 0.3 mg/mL, based on total volume of the oral liquid composition, or in any concentration or within any concentration range subsumed therein. In various non-limiting embodiments of the present oral liquid compositions, sucralose can be present in a concentration range of about 0.05 mg/mL to about 0.5 mg/mL, about 0.07 mg/mL to about 0.45 mg/mL, about 0.09 mg/mL to about 0.4 mg/mL, about 0.14 mg/mL to about 0.35 mg/mL, about 0.16 mg/mL to about 0.3 mg/mL, about 0.17 mg/mL to about 0.27 mg/mL, about 0.13 mg/mL to about 0.20 mg/mL, or about 0.15 mg/mL to about 0.25 mg/mL, based on the total volume of the liquid composition. In certain non-limiting embodiments of the present oral liquid compositions, sucralose can be present in a concentration of about 0.15 mg/mL, about 0.16 mg/mL, about 0.17 mg/mL, about 0.18 mg/mL, about 0.19 mg/mL, about 0.20 mg/mL, about 0.21 mg/mL, about 0.22 mg/mL, about 0.23 mg/mL, about 0.24 mg/mL, or about 0.25 mg/mL, based on total volume of the oral liquid composition.

One or more flavoring agents optionally can be included in the present oral liquid compositions to enhance the taste or aroma of the oral liquid compositions. Various suitable natural or synthetic flavoring agents can be selected from standard reference books, for example Fenaroli's Handbook of Flavor Ingredients, 3rd edition (1995). Suitable natural flavors for inclusion in the oral liquid composition, some of which can readily be simulated with synthetic agents or combinations thereof, include, but are not limited to, almond, anise, apple, apricot, bergamot, blackberry, blackcurrant, blueberry, cacao, caramel, cherry, cinnamon, clove, coffee, coriander, cranberry, cumin, dill, eucalyptus, fennel, fig, ginger, grape, grapefruit, guava, hop, lemon, licorice, lime, malt, mandarin, molasses, nutmeg, orange, peach, pear, peppermint, pineapple, raspberry, rose, spearmint, strawberry, tangerine, tea, tutti-frutti, vanilla, wintergreen, and the like. In various non-limiting embodiments, the oral liquid compositions herein can include cherry, grape, and/or bubblegum flavoring agents.

In various non-limiting embodiments of the oral liquid compositions according to the present disclosure, one or a combination of flavoring agents can be present in a total concentration range of about 0.5 mg/mL to about 3 mg/mL, based on the total volume of the oral liquid composition, or in any concentration or within any concentration range subsumed therein. In various non-limiting embodiments of the oral liquid composition according to the present disclosure, one or a combination of flavoring agents can be present in a total concentration range of about 0.5 mg/mL to about 1.0 mg/mL, about 0.5 mg/mL to about 1.1 mg/mL, about 0.5 mg/mL to about 1.2 mg/mL, about 0.5 mg/mL to about 1.3 mg/mL, about 0.5 mg/mL to about 1.4 mg/mL, about 0.5 mg/mL to about 1.5 mg/mL, about 0.5 mg/mL to about 1.6 mg/mL, about 0.5 mg/mL to about 1.7 mg/mL, about 0.5 mg/mL to about 1.8 mg/mL, about 0.5 mg/mL to about 1.9 mg/mL, about 0.5 mg/mL to about 2.0 mg/mL, about 0.5 mg/mL to about 2.1 mg/mL, about 0.5 mg/mL to about 2.2 mg/mL, about 0.5 mg/mL to about 2.3 mg/mL, about 0.5 mg/mL to about 2.4 mg/mL, about 0.5 mg/mL to about 2.5 mg/mL, about 0.5 mg/mL to about 2.6 mg/mL, about 0.5 mg/mL to about 2.7 mg/mL, about 0.5 mg/mL to about 2.8 mg/mL, about 0.5 mg/mL to about 2.9 mg/mL, about 1 mg/mL to about 2 mg/mL, about 1.2 mg/mL to about 2.0 mg/mL, about 1.4 mg/mL to about 2.0 mg/mL, about 1.6 mg/mL to about 2.0 mg/mL, or about 1.8 mg/mL to about 2.0 mg/mL, based on the volume of the oral liquid composition.

In various non-limiting embodiments, coloring agents may be included in the present oral liquid compositions for identification and/or aesthetic purposes. Suitable coloring agents can include, but are not limited to, FD&C Red No. 3, FD&C Red No. 20, FD&C Red No. 40, FD&C Yellow No. 6, FD&C Blue No. 2, D&C Green No. 5, D&C Orange No. 5, caramel, ferric oxide, or mixtures thereof. Other possible coloring agents will be apparent to those having ordinary skill.

Suitable liquid vehicles for use in oral liquid compositions according to the present disclosure can be selected based on their ability to impart desired qualities including, for example, clarity, nontoxicity, acceptable viscosity, compatibility with excipients, chemical inertness, palatability, acceptable odor and/or color, and economy. Exemplary liquid vehicles that may be included in embodiments of oral liquid compositions according to the present disclosure include, for example, water, ethyl alcohol, glycerin, propylene glycol, syrup (sugar or other sweetener based substance, e.g., ORA-SWEET™ SF sugar-free flavored syrup), juices (apple, grape, orange, cranberry, cherry, tomato and the like), other beverages (tea, coffee, soft drinks, milk and the like), oils (olive, soybean, corn, mineral, castor and the like), and combinations or mixtures thereof. Certain liquid vehicles, e.g., one or more oils and water, can be combined to form emulsions for inclusion in the oral liquid compositions. In various embodiments, water (e.g., purified water) is used as a vehicle in the oral liquid compositions. In various other embodiments, syrup and/or juice is used as a vehicle in the oral liquid compositions.

The oral liquid compositions disclosed herein can be homogenous. As used herein, a "homogenous liquid" refers to a liquid that is uniform in appearance, identity, consistency and drug concentration per volume. Non-homogenous liquids can include such liquids that have varied coloring, and/or viscosity, as well as non-uniform drug concentration in each unit volume. Homogeneity in liquids can be assessed by qualitative identification or appearance tests and/or quantitative high performance liquid chromatography (HPLC) testing or the like. Exemplary qualitative testing can include visual inspection of the resultant liquid for air bubbles and/or undissolved solids, which may cause variable dosing. Analytical HPLC testing can also determine drug concentration uniformity by examining aliquots of certain volume sections (e.g., 5 or 10 mL from the top, middle and bottom of a 150 mL bottle). The mixing methods and excipients disclosed herein can be selected to impart a homogenous quality to the oral liquid compositions.

Mixing methods used when preparing oral liquid compositions according to the present disclosure can encompass any type of mixing resulting in a homogenous oral liquid composition. Mixing can include one or more of stirring, shaking, swirling, agitating, or inverting. Individual components of the oral liquid composition can be added sequentially, concurrently, or in any combination thereof to a liquid vehicle. Individual components can be added sequentially, one at a time. The sequential addition of individual components can include mixing for a certain time interval after each or some of the sequential additions. All individual components can be added at the same time to a liquid vehicle and then mixed for a certain time interval.

Mixing can occur for certain time intervals, such as, for example and without limitation, about 10 seconds, about 20 seconds, about 30 seconds, about 40 seconds, about 50 seconds, about 60 seconds, about 90 seconds, about 2 minutes, about 2.5 minutes, about 3 minutes, about 3.5 minutes, about 4 minutes, about 4.5 minutes, about 5 minutes, about 6 minutes, about 7 minutes, about 8 minutes, about 9 minutes, or about 10 minutes or more. Mixing can occur in time interval ranges, for example and without limitation, from about 10 seconds to about 60 seconds, about 30 seconds to about 60 seconds, about 1 minute to about 10 minutes, about 3 minutes to about 7 minutes, or about 5 minutes to about 10 minutes. When there are two or more mixing steps, the time intervals for each mixing can be the same or different. The resulting oral liquid composition can be allowed to stand for a set amount of time, for example, about 5 minutes, about 10 minutes, about 20 minutes, about 30 minutes, about 40 minutes, about 50 minutes, about 60 minutes, about 90 minutes, about 120 minutes, or more to allow any resulting air bubbles arising from mixing to dissipate.

Stability

Embodiments of oral liquid compositions disclosed herein can be stable under various storage conditions. As used herein, the term "stable" may refer to the oral liquid composition retaining at least about 90% of an initial amount or concentration of amlodipine besylate in a volume of the oral liquid composition, retaining at least about 95% of an initial concentration or volume amlodipine besylate in a volume of the oral liquid composition at the end of a given time period stored under specified storage conditions, or retaining at least about 98% of an initial concentration or amount of amlodipine besylate in a volume of the oral liquid composition at the end of a given time period stored under specified storage conditions.

Oral liquid compositions according to the present disclosure comprising amlodipine besylate have been observed to exhibit unexpectedly improved stability. For example, it has been observed that embodiments of oral liquid compositions according to the present disclosure retain at least 90% of an initial concentration of amlodipine besylate (i.e., are stable) after the compositions have been stored for at least six months at standard conditions of 25° C.±2° C. and 60%±5% RH.

Also, it has been observed that embodiments of oral liquid compositions according to the present disclosure retain at least 90% of an initial concentration of amlodipine besylate after the compositions have been stored for at least six months at intermediate conditions of 20° C.±2° C. and 65%±5% RH It also has been observed that embodiments of oral liquid compositions according to the present disclosure retain at least 90% of an initial concentration of amlodipine besylate after the compositions have been stored for at least six months under refrigerated conditions of 5° C.±3° C.

In addition, it has been observed that embodiments of oral liquid compositions according to the present disclosure retain at least 90% of an initial concentration of amlodipine besylate after the compositions have been stored for at least three months under accelerated conditions of 40° C.±2° C. and not more than (NMT) 25% RH.

It also has been observed that certain embodiments of oral liquid compositions according to the present disclosure retain at least 90% of an initial concentration of amlodipine besylate after the compositions have been stored in a sealed container for nine months at 23° C. to 27° C. and 55% to 65% relative humidity.

In addition, it has been observed that certain embodiments of oral liquid compositions according to the present disclosure retain at least 90% of an initial concentration of amlodipine besylate after the compositions have been stored in a sealed container for nine months at 28° C. to 32° C. and 60% to 70% relative humidity.

Methods of Treatment, Dosing, and Administration

The present disclosure also is directed to methods of treatment comprising administering an oral liquid composition according to the present disclosure to a subject in need thereof. An oral liquid composition disclosed herein can be used in the treatment of conditions including, for example, hypertension, heart failure, and coronary artery disease. Hypertension, as used herein, includes both primary (essential) hypertension and secondary hypertension. Hypertension can be classified in cases when blood pressure values are greater than or equal to 140/90 (systolic/diastolic) mm Hg in an adult subject. In various embodiments, the oral liquid compositions disclosed herein can be used in treating primary (essential) hypertension in a subject. In various embodiments, the oral liquid composition disclosed herein can be used in treating secondary hypertension in a subject. In various embodiments, the subject can be a pediatric subject. Pediatric hypertension can be classified in cases where the child's blood pressure is greater than the 95th percentile for the patient's age, sex and height. In various embodiments, the subject can be a geriatric subject. Hypertension in geriatric patients can be defined in a manner similar to that in adult patients, i.e., blood pressure values greater than or equal to 140/90 (systolic/diastolic) mm Hg.

The oral liquid compositions disclosed herein can be used for the treatment of diseases and conditions disclosed herein. In addition, a method for treating any of the diseases or conditions disclosed herein for a subject in need of such treatment involves administration of therapeutically effective amounts of the oral liquid compositions disclosed herein to the subject.

Dosages of the oral liquid compositions disclosed herein can be determined by any suitable method. Maximum tolerated dose (MTD) and maximum response dose (MRD) for amlodipine besylate can be determined via established animal and human experimental protocols. For example, toxicity and therapeutic efficacy of amlodipine besylate can be determined by standard pharmaceutical procedures in cell cultures or experimental animals, including, but not limited to, determination of the $LD_{50}$ (the dose lethal to 50% of the population) and the $ED_{50}$ (the dose therapeutically effective in 50% of the population). The dose ratio between the toxic and therapeutic effects is known as the therapeutic index, and it can be expressed as a ratio between $LD_{50}$ and $ED_{50}$.

Amlodipine besylate dosages exhibiting high therapeutic indices are desirable. The data obtained from cell culture assays and animal studies can be used in formulating a range of dosage for use in humans. The dosage of such compounds lies preferably within a range of circulating concentrations that include the $ED_{50}$ with minimal toxicity. The dosage may vary within this range depending upon the dosage form employed and the route of administration utilized. Additional relative dosages, represented as a percent of maximal response or of maximum tolerated dose, are readily obtained via these protocols.

The oral liquid composition can be provided for administration to a human subject at a maximum tolerated dose (MTD) of amlodipine besylate. The amount of amlodipine besylate in a volume of oral liquid composition administered to a human subject can be from about 10% to about 90% of the MTD, from about 25% to about 75% of the MTD, or about 50% of the MTD. The amount of amlodipine besylate in a volume of the oral liquid composition administered to a human subject can range from about 20% to about 80% of the MTD, about 30% to about 70% of the MTD, about 40% to about 60% of the MTD, or about 20% to about 60% of the MTD. The amount of amlodipine besylate in a volume of the oral liquid composition administered can be at least about 5%, 10%, 15%, 20%, 25%, 30%, 35%, 40%, 45%, 50%, 55%, 60%, 65%, 70%, 75%, 80%, 85%, 90%, 95%, 99%, or 100%, or any other suitable percentage, of the MTD for amlodipine besylate.

The amount of amlodipine besylate in a volume of the oral liquid composition administered to a subject can be similar, comparable, or equivalent to a dosage of a known amlodipine besylate tablet formulation. The oral liquid composition can be provided in a dosage that provides similar, comparable, or equivalent pharmacokinetic parameters (e.g., AUC, $C_{max}$, $T_{max}$, $C_{min}$, $T_{1/2}$) as a dosage of a commercially available amlodipine besylate tablet formulation. Similar, comparable, or equivalent pharmacokinetic parameters, in some instances, refer to within 80% to 125%, 80% to 120%, 85% to 125%, 90% to 110%, or increments therein, of the given values. It should be recognized that the ranges can, but need not be, symmetrical, e.g., 85% to 105%.

The oral liquid compositions disclosed herein can be administered at a dosage disclosed herein or at other appropriate dose levels contemplated by a medical practitioner. The oral liquid compositions disclosed herein can be administered for prophylactic and/or therapeutic treatments. The oral liquid compositions can be administered to a patient already suffering from an indication, e.g., hypertension, in a therapeutically effective amount sufficient to cure the disease or at least partially arrest or ameliorate the symptoms, e.g., lower blood pressure. Amounts effective for this use depend on, for example, the age of the patient, severity of the disease, previous therapy, the patient's health status, weight, and response to the oral liquid compositions, and are within the judgment of the treating physician. Therapeutically effective amounts are optionally determined by methods including, but not limited to, a dose escalation clinical trial.

If a patient's condition does not improve, upon the doctor's discretion, the oral liquid composition disclosed herein can be administered chronically, that is, for an extended period, to ameliorate or otherwise control or limit the symptoms of the patient's disease. Administration of the oral liquid composition can continue until complete or partial response of a disease occurs.

According to certain non-limiting embodiments, amlodipine besylate can be administered over a dose range of 2 mg to 10 mg daily for treating adult hypertension. A suitable volume of an oral liquid composition according to the present disclosure can be administered to a subject in need to provide the predetermined dosage for treating adult hypertension.

According to certain non-limiting embodiments, amlodipine besylate can be administered over a dose range of 2 mg to 5 mg daily for treating pediatric hypertension. A suitable volume of an oral liquid composition according to the present disclosure can be administered to a subject in need to provide the predetermined dosage for treating pediatric hypertension.

According to certain non-limiting embodiments, amlodipine besylate can be administered over a dose range of 2 mg to 5 mg daily, or 5 mg to 10 mg daily, or 2 mg to 5 mg daily for treating heart failure. A suitable volume of an oral liquid composition according to the present disclosure can be administered to a subject in need to provide the predetermined dosage for treating heart failure.

According to certain non-limiting embodiments, amlodipine besylate can be administered over a dose range of 2 mg to 10 mg daily, or 5 mg to 10 mg daily, or 2 mg to 5 mg daily for treating coronary artery disease. A suitable volume of an oral liquid composition according to the present disclosure can be administered to a subject in need to provide the predetermined dosage for treating coronary artery disease.

An oral liquid composition disclosed herein can be administered to a subject who is in a fasted state. A fasted state refers to the state of a subject who has gone without food or fasted for a specified amount of time. General fasting periods can include at least 4 hours, at least 6 hours, at least 8 hours, at least 10 hours, at least 12 hours, at least 14 hours, and at least 16 hours without food. An oral liquid composition disclosed herein can be administered to a subject who has fasted overnight.

An oral liquid composition disclosed herein can be administered to a subject who is in a fed state. A fed state refers to the state of a subject who has taken food or has had a meal. An oral liquid composition can be administered to a subject in a fed state 5 minutes post-meal, 10 minutes post-meal, 15 minutes post-meal, 20 minutes post-meal, 30 minutes post-meal, 40 minutes post-meal, 50 minutes post-meal, 1 hour post-meal, 2 hours post-meal, or more. An oral liquid composition can be administered to a subject along with food.

NON-LIMITING EXAMPLES

Example 1. Preparation of Oral Liquid Compositions Comprising Amlodipine Besylate Two oral liquid compositions #1 and #2 were prepared using the method described below. The ingredients in the compositions are provided in Table 1.

TABLE 1

Compositions of oral liquid compositions #1 and #2, both oral liquid compositions comprising, by weight, 0.1% amlodipine besylate (1 mg/mL).

| Ingredient | #1 % w/v | #2 % w/v | #1 mg/mL | #2 mg/mL |
|---|---|---|---|---|
| Amlodipine Besylate, USP | 0.1 | 0.1 | 1 | 1 |
| Hydroxypropyl β-Cyclodextrin | 5.0 | — | 50 | — |
| β-Cyclodextrin | 1.0 | — | 10 | |
| Methylparaben | 0.2 | 0.2 | 2 | 2 |

TABLE 1-continued

Compositions of oral liquid compositions #1 and #2, both oral liquid compositions comprising, by weight, 0.1% amlodipine besylate (1 mg/mL).

| Ingredient | #1 % w/v | #2 % w/v | #1 mg/mL | #2 mg/mL |
|---|---|---|---|---|
| Grape Flavor | 0.1 | 0.1 | 1 | 1 |
| Sucralose | 0.02 | 0.02 | 0.2 | 0.2 |
| Purified Water, USP | 94.58 | 98.58 | 945.8 | 985.8 |

In preparing oral liquid compositions #1 and #2, hydroxypropyl β-cyclodextrin (composition #1) or β-cyclodextrin (composition #2) was added to a volume of purified water and mixed until completely dissolved. Next, methyl paraben was added to the solution and dissolved completely under mixing. Sucralose was then added to the solution and completely dissolved under mixing. Next, amlodipine besylate was added to the solution and completely dissolved under mixing. Grape flavor was added, and purified water was then added quantum satis as indicated in Table 1. All steps were performed at room temperature, and all components were added in the quantities/concentrations needed to provide the final concentrations in the compositions listed in Table 1.

Example 2. Preparation of Oral Liquid Compositions Comprising Amlodipine Besylate and Curcumin Two oral liquid compositions #3 and #4 were prepared using the method described below. The ingredients in the compositions are provided in Table 2.

TABLE 2

Compositions of oral liquid compositions #3 and #4, both oral liquid compositions comprising, by weight, 0.1% amlodipine besylate (1 mg/mL) and curcumin.

| Ingredient | #3 % w/v | #4 % w/v | #3 mg/mL | #4 mg/mL |
|---|---|---|---|---|
| Amlodipine Besylate, USP | 0.1 | 0.1 | 1 | 1 |
| Curcumin solution (0.03% w/w curcumin in 99.97% w/w Propylene Glycol) | 20 | 20 | 200 | 200 |
| Hydroxypropyl β-Cyclodextrin | 5.0 | — | 50 | — |
| β-Cyclodextrin | 1.0 | — | 10 | — |
| Methylparaben | 0.2 | 0.2 | 2 | 2 |
| N&A Orange | 0.1 | 0.1 | 1 | 1 |
| Sucralose | 0.02 | 0.02 | 0.2 | 0.2 |
| Purified Water | 74.58 | 78.58 | 745.8 | 785.8 |

In preparing oral liquid compositions #3 and #4, hydroxypropyl β-cyclodextrin (composition #3) or β-cyclodextrin (composition #4) was added to a volume of purified water and mixed until completely dissolved. Next, methyl paraben was added to the solution and dissolved completely under mixing. Sucralose was then added to the solution and completely dissolved under mixing. Next, the curcumin solution (0.03% w/w curcumin in 99.97% w/w propylene glycol) was added to the solution and completely dissolved under mixing. Amlodipine besylate was then added to the solution and completely dissolved under mixing. Orange flavor was added, and purified water was then added quantum satis as indicated in Table 2. All steps were performed at room temperature, and all components were added in the quantities/concentrations needed to provide the final concentrations in the compositions listed in Table 2.

Example 3. Stability Study of Oral Liquid Compositions #1 and #2

Figure 2A:
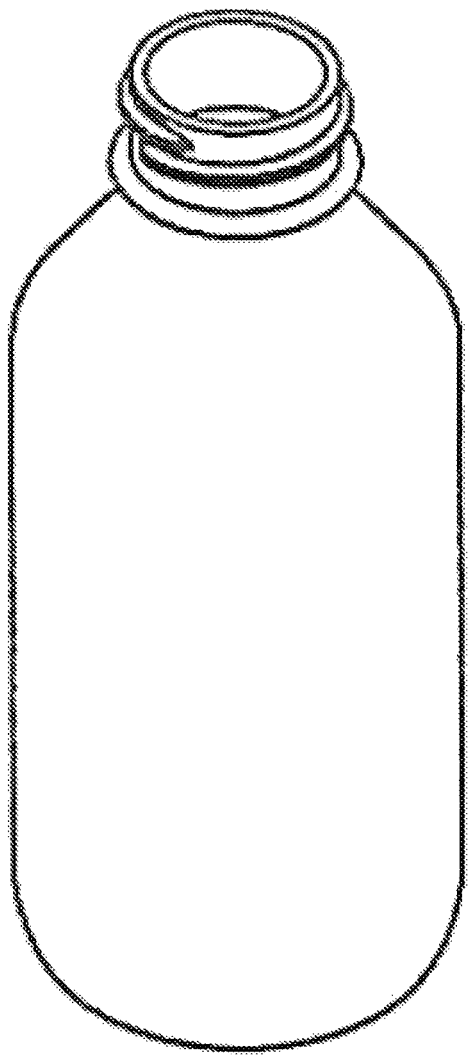
Figure 2B:
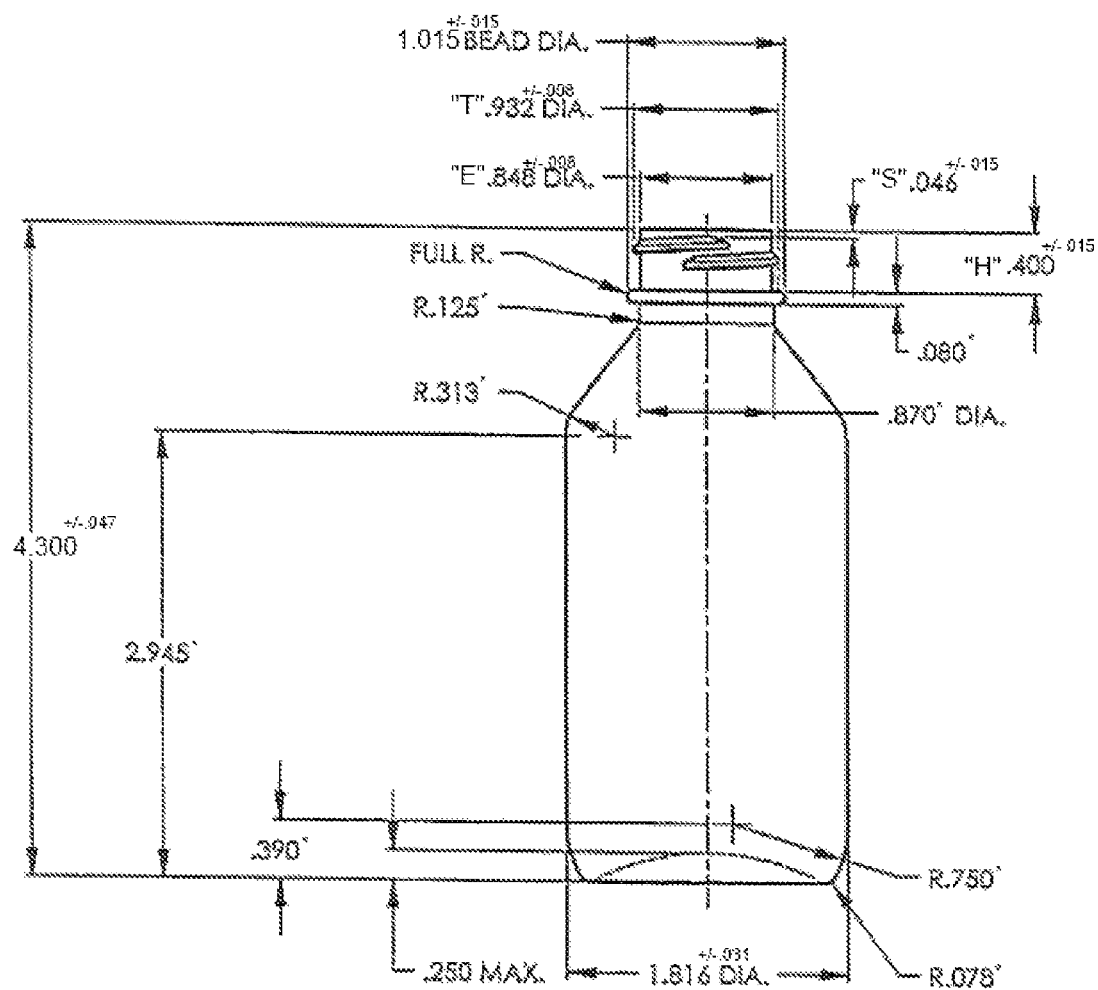
Figure 2C:
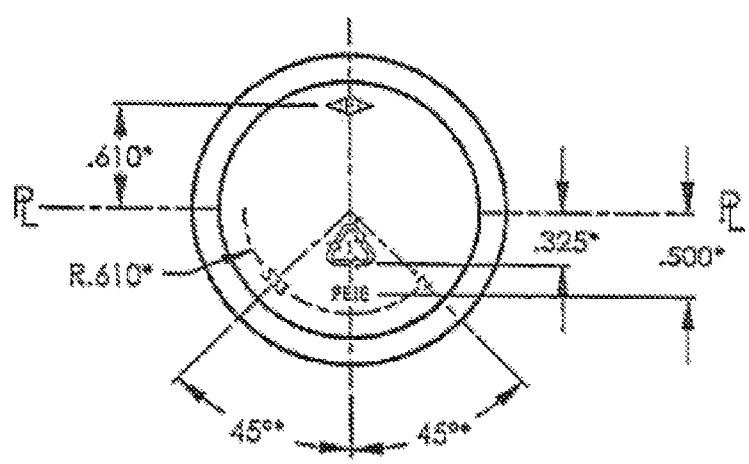
Figure 3A:
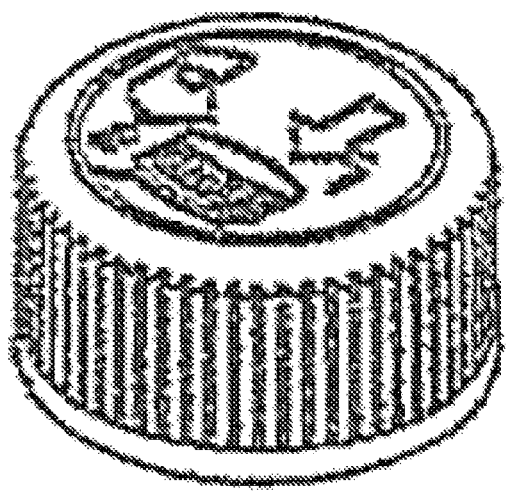
Figure 3B:
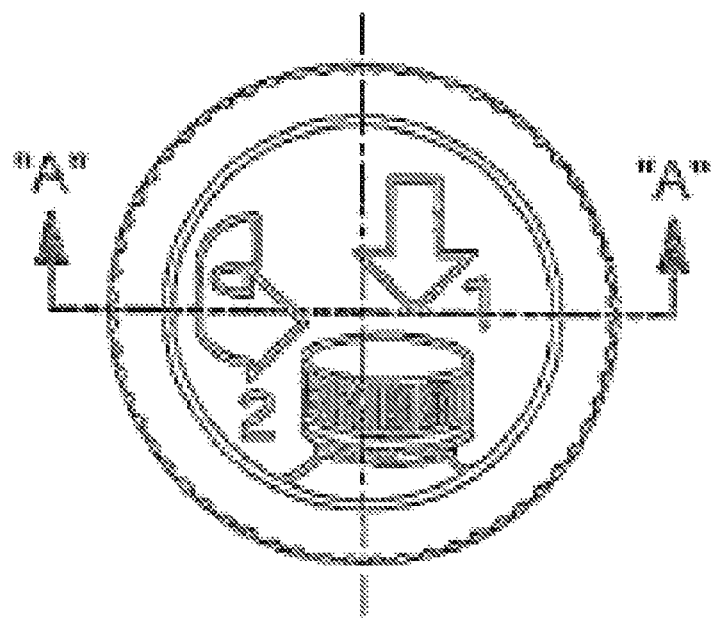
Figure 3C:
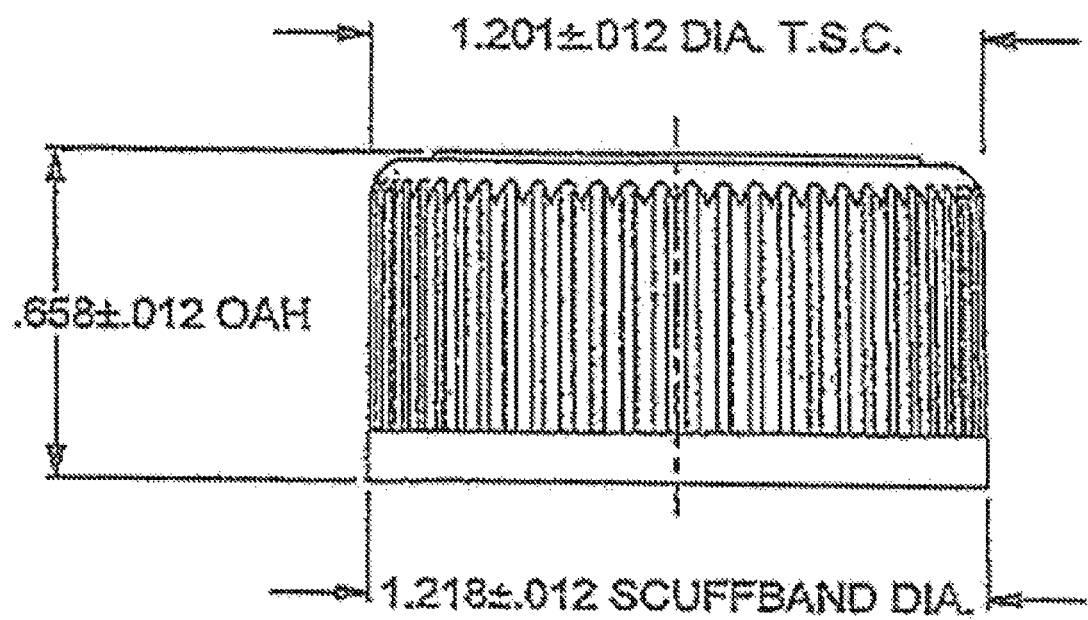
Figure 3D:
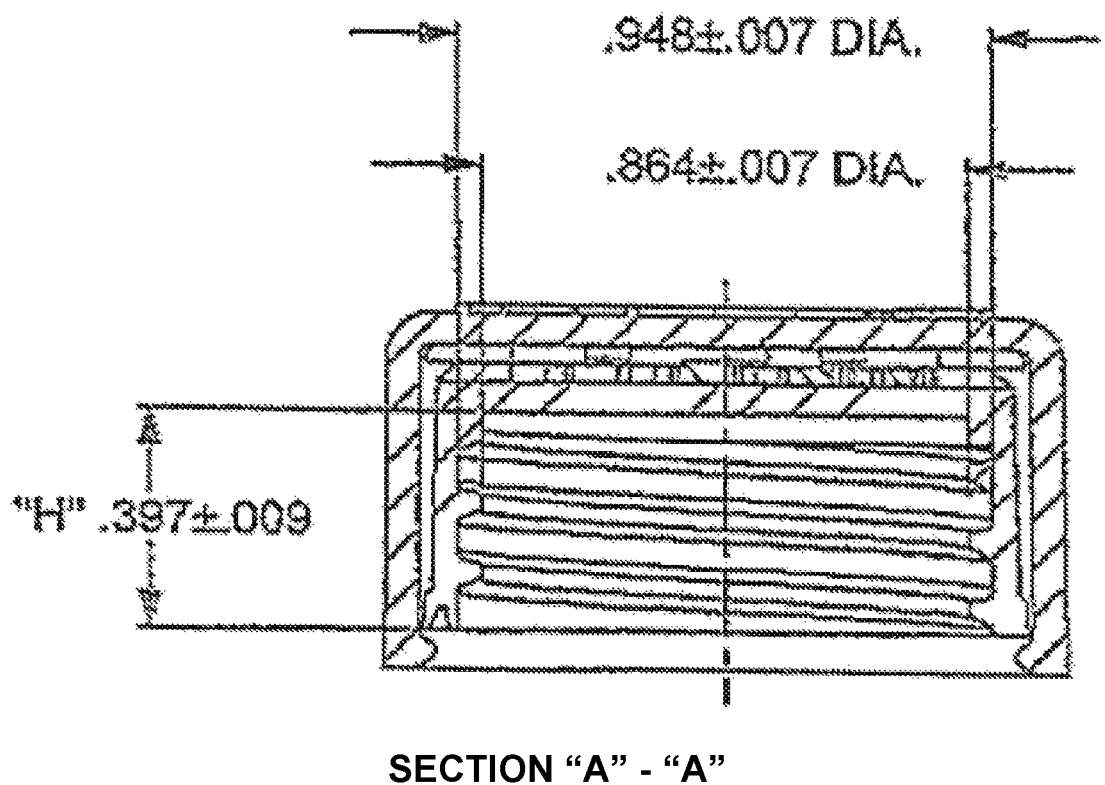

For purposes of conducting a stability study, 120 mL samples of each of oral liquid compositions #1 and #2 of Example 1 were packaged separately in identical container closure systems. Each container closure system, as shown in FIGS. 2A-2C, included a 4 ounce (120 mL), Boston round white (colorant: white 11078 AMPACET), high density polyethylene ("HDPE") (resin: MARLEX HEIM 5502BN) bottle. As shown in FIGS. 3A-3D, each container closure system also included a 24 mm SECURX™ ribbed side pictorial top (resin: INEOS H20E-00), white closure (colorant: white 11343 AMPACET), with a foam liner (liner: SELIG SEALING 0.035" C25 FSLE5-9). Samples were stored in the container closure systems upright in a calibrated stability chamber under one of the following storage conditions: refrigerated conditions ("REF") of 5° C.±3° C.; standard or controlled room temperature conditions ("CRT") of 25° C.±2° C. and 60%±5% relative humidity (RH); intermediate conditions ("INT") of 35° C.±2° C. and 65%±5% RH; and accelerated conditions ("ACC") of 40° C.±2° C. and not more than (NMT) 25% RH. Samples of the oral liquid compositions stored in the calibrated stability chamber were taken from the containers at set time intervals to assay for amlodipine besylate. Samples were analyzed using a high performance liquid chromatography (HPLC) system Table 3 reports the stability data for oral liquid compositions #1 and #2, stored under refrigerated conditions (5° C.±3° C.) and in the sealed container closure system, at 3 and 6 month time intervals. The stability assay percentages for amlodipine besylate listed in Table 3, as well as in Tables 4-10 and 15-18 below, are percentages of the particular composition's 1 mg/mL concentration of amlodipine besylate measured based on the assay. Thus, for example, in Table 3 the "Initial" assayed concentration of amlodipine besylate in Composition #1 was 97.2% of the 1 mg/mL concentration for amlodipine besylate listed in Table 1. This difference occurred at least in part because the assays were performed weight per weight, rather than weight/volume, and some minor variations from actual concentrations were expected.

TABLE 3

Stability assay for oral liquid compositions #1 and #2 tested under refrigerated conditions (5° ± 3° C.) and stored in container closure system.

| Time | Composition #1 (% amlodipine besylate) | Composition #2 (% amlodipine besylate) |
|---|---|---|
| Initial | 97.2 | 97.4 |
| 3 months | 107.7 | NA* |
| 6 months | 99.9 | 99.9 |

*NA = Not Assayed

As indicated in Table 3, oral liquid compositions #1 and #2 of Example 1 were stable for at least 6 months when stored under refrigerated (REF) conditions in the sealed container closure system. The stability assay showed that 99.9% of the original amlodipine besylate was retained in the oral liquid composition #1 in the sealed container closure system over the course of the refrigerated stability conditions assay for 6 months. The stability assay also showed that 99.9% of the original amlodipine besylate was retained in the oral liquid composition #2 in the sealed container closure system over the course of the refrigerated stability conditions assay for 6 months.

Table 4 reports the stability data for oral liquid compositions #1 and #2, stored under standard conditions (25° C.±2° C. and 60%±5% RH) in the sealed container closure system, at 3 and 6 month time intervals.

TABLE 4

Stability assay for oral liquid compositions #1 and #2 tested under standard conditions (25° C. ± 2° C. and 60% ± 5% RH) and stored in container closure system.

| Time | Composition #1 (% amlodipine besylate) | Composition #2 (% amlodipine besylate) |
| --- | --- | --- |
| Initial | 97.2 | 97.4 |
| 3 months | 100.2 | 98.7 |
| 6 months | 93.4 | 90.0 |

As indicated in Table 4, oral liquid compositions #1 and #2 of Example 1 were stable for at least 6 months when stored under standard conditions (25° C.±2° C. and 60%±5% RH) in the sealed container closure system. The stability assay showed that 93.4% of the original amlodipine besylate was retained in oral liquid composition #1 in the sealed container closure system over the course of the standard stability conditions assay for 6 months. The stability assay also showed that 90.0% of the original amlodipine besylate was retained in oral liquid composition #2 in the sealed container closure system over the course of the standard stability conditions assay for 6 months.

Table 5 reports the stability data for oral liquid compositions #1 and #2, tested under intermediate conditions (30° C.±2° C. and 65%±5% RH) in the sealed container closure system, at 3 and 6 month time intervals.

TABLE 5

Stability assay for oral liquid compositions #1 and #2 tested under intermediate conditions (30° C. ± 2° C. and 65% ± 5% RH) and stored in container closure system.

| Time | Composition #1 (% amlodipine besylate) | Composition #2 (% amlodipine besylate) |
| --- | --- | --- |
| Initial | 97.2 | 97.4 |
| 3 months | 98.5 | 95.5 |
| 6 months | 88.7 | 82.0 |

As indicated in Table 5, oral liquid compositions #1 and #2 of Example 1 were stable for at least 3 months when stored under intermediate conditions (30° C.±2° C. and 65%±5% RH) in the sealed container closure system. The stability assay showed that 98.5% of the original amlodipine besylate was retained in oral liquid composition #1 in the container closure system over the course of the intermediate stability conditions assay for 3 months. The stability assay also showed that 95.5% of the original amlodipine besylate was retained in oral liquid composition #2 in the container closure system over the course of the intermediate stability conditions assay for 3 months. However, the study showed that compositions #1 and #2 were not stable for at least 6 months under the intermediate conditions. The compositions #1 and #2 retained 88.7% and 82.0%, respectively, of the original amlodipine besylate when sampled at 6 months after storage in the sealed container closure system in intermediate conditions.

Table 6 reports the stability data for oral liquid compositions #1 and #2 stored under accelerated conditions (40° C.±2° C. and NMT 25% RH) in the sealed container closure system, at 1, 3, and 6 month time intervals.

TABLE 6

Stability assay for oral liquid compositions #1 and #2 tested under accelerated conditions (40° C. ± 2° C. and NMT 25% RH) and stored in container closure system.

| Time | Composition #1 (% amlodipine besylate) | Composition #2 (% amlodipine besylate) |
| --- | --- | --- |
| Initial | 97.2 | 97.4 |
| 1 month | NA* | NA |
| 3 months | 93.3 | 79.9 |
| 6 months | NA | 50.0 |

*NA = Not Assayed

As indicated in Table 6, oral liquid composition #1 of Example 1 was stable for at least 3 months when stored under accelerated conditions (40° C.±2° C. and NMT 25% RH) in the 4 oz. HDPE bottles of the container closure system. The stability assay showed that 93.3% of the original amlodipine besylate was retained in the oral liquid composition #1 over the course of the accelerated stability conditions assay for 6 months.

As indicated in Table 6, oral liquid composition #2 of Example 1 was not stable for at least 3 months when stored under accelerated conditions (40° C.±2° C. and NMT 25% RH) in the sealed container closure system. The stability assay showed that 79.9% of the original amlodipine besylate was retained in the oral liquid composition #2 in the sealed container closure system over the course of the accelerated stability conditions assay for 3 months.

Example 4. Stability Study of Oral Liquid Compositions #3 and #4

For purposes of conducting a stability study, 120 mL of oral liquid compositions #3 and #4 of Example 2 were packaged separately in the sealed container closure system.

The container closure system included the same container and closure as used in the stability study of Example 3. Samples were stored upright in the calibrated stability chamber under the storage conditions used in Example 3: refrigerated conditions of 5° C.±3° C.; standard or controlled room temperature conditions of 25° C.±2° C. and 60%±5% RH; intermediate conditions of 35° C.±2° C. and 65%±5% RH; and accelerated conditions of 40° C.±2° C. and not more than (NMT) 25% RH. The assay was conducted as in Example 3, with samples taken at set time intervals to assay for amlodipine besylate.

Table 7 reports the stability data for oral liquid compositions #3 and #4, stored under refrigerated conditions (5° C.±3° C.) and in the sealed container closure system, at 3 and 6 month time intervals.

TABLE 7

Stability assay for oral liquid compositions #3 and #4 tested under refrigerated conditions (5° ± 3° C.) and stored in container closure system.

| Time | Composition #3 (% amlodipine besylate) | Composition #4 (% amlodipine besylate) |
| --- | --- | --- |
| Initial | 97.1 | 97.9 |
| 3 months | 107.1 | 106.3 |
| 6 months | 101.2 | 95.2 |

As indicated in Table 7, oral liquid compositions #3 and 4 of Example 2 were stable for at least 6 months when stored under refrigerated (REF) conditions in the sealed container closure system. The stability assay showed that 101.2% of the original amlodipine besylate was retained in the oral liquid composition #3 in the sealed container closure system over the course of the refrigerated stability conditions assay for 6 months. The stability assay also showed that 95.2% of the original amlodipine besylate was retained in the oral liquid composition #4 in the sealed container closure system over the course of the refrigerated stability conditions assay for 6 months.

Table 8 reports the stability data for oral liquid compositions #3 and #4, stored under standard conditions (25° C.±2° C. and 60%±5% RH) and in the sealed container closure system, at 3 and 6 month time intervals.

TABLE 8

Stability assay for oral liquid compositions #3 and #4 tested under standard conditions (25° C. ± 2° C. and 60% ± 5% RH) and stored in container closure system.

| Time | Composition #3 (% amlodipine besylate) | Composition #4 (% amlodipine besylate) |
| --- | --- | --- |
| Initial | 97.1 | 97.9 |
| 3 months | 105.8 | 104.3 |
| 6 months | 98.4 | 98.3 |

As indicated in Table 8, oral liquid compositions #3 and #4 of Example 2 were stable for at least 6 months when stored under standard conditions of 25° C.±2° C. and 60%±5% RH in the sealed container closure system. The stability assay showed that 98.4% of the original amlodipine besylate was retained in oral liquid composition #3 in the sealed container closure system over the course of the standard stability conditions assay for 6 months. The stability assay also showed that 98.3% of the original amlodipine besylate was retained in oral liquid composition #4 in the sealed container closure system over the course of the standard stability conditions assay for 6 months.

Table 9 reports the stability data for oral liquid compositions #3 and #4, tested under intermediate conditions (30° C.±2° C. and 65%±5% RH) in the sealed container closure system, at 3 and 6 month time intervals.

TABLE 9

Stability assay for oral liquid compositions #3 and #4 tested under intermediate conditions (30° C. ± 2° C. and 65% ± 5% RH) and stored in container closure system.

| Time | Composition #3 (% amlodipine besylate) | Composition #4 (% amlodipine besylate) |
| --- | --- | --- |
| Initial | 97.1 | 97.9 |
| 3 months | 102.9 | 101.1 |
| 6 months | 96.2 | 93.6 |

As indicated in Table 9, oral liquid compositions #3 and #4 of Example 2 were stable for at least 6 months when stored under intermediate conditions (30° C.±2° C. and 65%±5% RH) in the sealed container closure system. The stability assay showed that 96.2% of the original amlodipine besylate was retained in oral liquid composition #3 in the sealed container closure system over the course of the intermediate stability conditions assay for 6 months. The stability assay also showed that 93.6% of the original amlodipine besylate was retained in oral liquid composition #4 in the sealed container closure system over the course of the intermediate stability conditions assay for 6 months.

Table 10 reports the stability data for oral liquid compositions #3 and #4, tested under accelerated conditions (40° C.±2° C. and NMT 25% RH) in the sealed container closure system, at 1, 3, and 6 month time intervals.

TABLE 10

Stability assay for oral liquid compositions #3 and #4 tested under accelerated conditions (40° C. ± 2° C. and NMT 25% RH) and stored in container closure system.

| Time | Composition #3 (% amlodipine besylate) | Composition #4 (% amlodipine besylate) |
| --- | --- | --- |
| Initial | 97.1 | 97.9 |
| 1 month | 95.3 | 93.8 |
| 3 months | 96.7 | 94.5 |
| 6 months | 88.4 | 80.5 |

As indicated in Table 10, oral liquid composition #3 of Example 2 was stable for at least 3 months when stored under accelerated conditions (40° C.±2° C. and NMT 25% RH) in the sealed container closure system. The stability assay showed that 96.7% of the original amlodipine besylate was retained in the oral liquid composition #3 in the sealed container closure system over the course of the accelerated stability conditions assay for 3 months.

As indicated in Table 10, oral liquid composition #4 of Example 2 was stable for at least 3 months when stored under accelerated conditions (40° C.±2° C. and NMT 25% RH) in the sealed container closure system. The stability assay showed that 94.5% of the original amlodipine besylate was retained in the oral liquid composition #4 in the sealed container closure system over the course of the accelerated stability conditions assay for 3 months.

It will be apparent from the data herein that an unexpectedly significant difference in the stability of compositions #1 and #2 on the one hand, and compositions #3 and #4 on the other, was observed when the compositions were stored at intermediate and accelerated conditions. The significantly improved stability of compositions #3 and #4 under intermediate and accelerated conditions is believed to be at least partially attributable to the curcumin present in compositions #3 and #4. The curcumin apparently acted to stabilize the amlodipine besylate in those compositions when stored under those conditions over time.

Example 5. Preparation of Oral Liquid Compositions Comprising Amlodipine Besylate Three oral liquid compositions #5, #6, and #7 comprising 1 mg/mL amlodipine besylate were prepared. The ingredients in the compositions are provided in Tables 11 to 14. The composition of the curcumin solution that is an ingredient of oral liquid composition #6 is shown in Table 13.

TABLE 11

Composition of oral liquid compositions #5.

| Ingredient | % w/w | mg/mL | g/batch |
| --- | --- | --- | --- |
| Amlodipine Besylate, USP | 0.10 | 1.00 | 2.0 |
| Hydroxypropyl β-Cyclodextrin | 5.00 | 50.00 | 150.0 |

TABLE 11-continued

Composition of oral liquid compositions #5.

| Ingredient | % w/w | mg/mL | g/batch |
|---|---|---|---|
| Methylparaben, NF | 0.2 | 2.00 | 6.0 |
| Sucralose | 0.02 | 0.20 | 0.6 |
| Purified Water, USP | q.s. | q.s. | q.s. |
| TOTAL | 100.00 | 1000.00 | 2000.00 |

TABLE 12

Composition of oral liquid compositions #6.

| Ingredient | % w/w | mg/mL | g/batch |
|---|---|---|---|
| Amlodipine Besylate, USP | 0.10 | 1.00 | 4.14 |
| Curcumin solution (0.03% w/w curcumin in 99.97% w/w Propylene Glycol) | 20 | 200.00 | 600.0 |
| Hydroxypropyl β-Cyclodextrin | 5 | 50.00 | 150.0 |
| Methylparaben, NF | 0.2 | 2.00 | 6.0 |
| Sucralose | 0.02 | 0.20 | 0.6 |
| Purified Water, USP | q.s. | q.s. | q.s. |
| TOTAL | 100.00 | 1000.00 | 3000.00 |

TABLE 13

Composition of curcumin solution in oral liquid composition #6.

| Ingredient | % w/w | mg/mL | g/batch |
|---|---|---|---|
| Propylene Glycol, NF | 99.97 | 999.70 | 599.82 |
| Curcumin | 0.03 | 0.30 | 0.18 |
| TOTAL | 100.00 | 1000.00 | 600.00 |

TABLE 14

Composition of oral liquid compositions #7.

| Ingredient | % w/w | mg/mL | g/batch |
|---|---|---|---|
| Amlodipine Besylate, USP | 0.10 | 1.00 | 4.14 |
| Hydroxypropyl β-Cyclodextrin | 5 | 50.00 | 150.0 |
| Methylparaben, NF | 0.2 | 2 | 0.6 |
| Sucralose | 0.02 | 0.20 | 0.2 |
| FD&C Yellow No. 5 | 0.01 | 0.10 | 0.3 |
| Purified Water, USP | q.s. | q.s. | q.s. |
| TOTAL | 100.00 | 1000.00 | 3000.00 |

In preparing each of oral liquid compositions #5, #6, and #7, hydroxypropyl β-cyclodextrin was added to a volume of purified water and mixed until completely dissolved. Next, methylparaben was added to the solution and dissolved completely under mixing. Sucralose was then added to the solution and completely dissolved under mixing. With respect to composition #6, in a next step the curcumin solution (0.03% w/w curcumin in 99.97% w/w propylene glycol) was added to the solution and completely dissolved under mixing. With respect to composition #7, in a next step FD&C Yellow #5 was added to the solution and completely dissolved under mixing. Amlodipine besylate was then added to each of the three compositions and completely dissolved under mixing. Purified water was then added quantum satis as indicated in Tables 12-14. All steps were performed at room temperature, and all components were added in the quantities/concentrations needed to provide the final concentrations in the compositions listed in Table 11-14.

Example 6. Stability Study of Oral Liquid Compositions #5, #6, and #7

For purposes of conducting a stability study, 120 mL of oral liquid compositions #5, #6, and #7 of Example 5 were packaged separately in the sealed container closure system. The container closure system included the same container and closure as used in the stability study of Example 3. Samples were stored upright in a calibrated stability chamber under the storage conditions used in Example 3: refrigerated conditions of 5° C.±3° C.; standard or controlled room temperature conditions of 25° C.±2° C. and 60%±5% RH; intermediate conditions of 35° C.±2° C. and 65%±5% RH; and accelerated conditions of 40° C.±2° C. and not more than (NMT) 25% RH. The assay was conducted as in Example 3, with samples taken at set time intervals to assay for amlodipine besylate.

Table 7 reports the stability data for oral liquid compositions #5, #6, and #7, stored under refrigerated conditions (5° C.±3° C.) and in the sealed container closure system, for a 3 month time interval.

TABLE 15

Stability assay for oral liquid compositions #5, #6, and #7 tested under refrigerated conditions (5° ± 3° C.) and stored in container closure system.

| Time | Composition #5 (% amlodipine besylate) | Composition #6 (% amlodipine besylate) | Composition #7 (% amlodipine besylate) |
|---|---|---|---|
| Initial | 101.2 | 97.6 | 99.5 |
| 3 months | — | 97.0 | 97.8 |

As indicated in Table 15, oral liquid compositions #6 and #7 were stable for at least 3 months when stored under refrigerated (REF) conditions in the sealed container closure system. The stability assay showed that 97.0% of the original amlodipine besylate was retained in the oral liquid composition #6 in the sealed container closure system over the course of the refrigerated stability conditions assay for 3 months. The stability assay also showed that 97.8% of the original amlodipine besylate was retained in the oral liquid composition #7 in the sealed container closure system over the course of the refrigerated stability conditions assay for 3 months. The addition of the curcumin solution in composition #6 did not appear to improve the stability of the composition relative to composition #7 under refrigerated condition at the 3-month time interval based on the results of the assay.

Table 16 reports the stability data for oral liquid compositions #5, #6, and #7, stored under standard conditions (25° C.±2° C. and 60%±5% RH) and in the sealed container closure system, at a 3 month interval.

TABLE 16

Stability assay for oral liquid compositions #5, #6, and #7 tested under standard conditions (25° C. ± 2° C. and 60% ± 5% RH) and stored in container closure system.

| Time | Composition #5 (% amlodipine besylate) | Composition #6 (% amlodipine besylate) | Composition #7 (% amlodipine besylate) |
|---|---|---|---|
| Initial | 101.2 | 97.6 | 99.5 |
| 3 months | 101.6 | 97.8 | 94.9 |

As indicated in Table 16, oral liquid compositions #5, #6, and #7 were stable for at least 3 months when stored under standard conditions of 25° C.±2° C. and 60%±5% RH in the sealed container closure system. The stability assay showed that 101.6% of the original amlodipine besylate was retained in oral liquid composition #5 in the sealed container closure system over the course of the standard stability conditions assay for 3 months. The stability assay also showed that 97.8% of the original amlodipine besylate was retained in oral liquid composition #6 in the sealed container closure system over the course of the standard stability conditions assay for 3 months. The stability assay additionally showed that 94.9% of the original amlodipine besylate was retained in oral liquid composition #7 in the sealed container closure system over the course of the standard stability conditions assay for 3 months. The addition of the curcumin solution in composition #6 did not appear to improve the stability of the composition relative to compositions #5 and #7 under standard condition at the 3-month time interval based on the results of the assay.

Table 17 reports the stability data for oral liquid compositions #5, #6, and #7, tested under intermediate conditions (30° C.±2° C. and 65%±5% RH) in the sealed container closure system, at a 3 month time interval.

TABLE 17

Stability assay for oral liquid compositions #5, #6, and #7 tested under intermediate conditions (30° C. ± 2° C. and 65% ± 5% RH) and stored in container closure system.

| Time | Composition #5 (% amlodipine besylate) | Composition #6 (% amlodipine besylate) | Composition #7 (% amlodipine besylate) |
|---|---|---|---|
| Initial | 101.2 | 97.6 | 99.5 |
| 3 months | 99.8 | 93.4 | 92.8 |

As indicated in Table 17, oral liquid compositions #5, #6, and #7 were stable for at least 3 months when stored under intermediate conditions (30° C.±2° C. and 65%±5% RH) in the sealed container closure system. The stability assay showed that 101.6% of the original amlodipine besylate was retained in oral liquid composition #5 in the sealed container closure system over the course of the intermediate stability conditions assay for 3 months. The stability assay also showed that 93.4% of the original amlodipine besylate was retained in oral liquid composition #6 in the sealed container closure system over the course of the intermediate stability conditions assay for 3 months. The stability assay additionally showed that 92.8% of the original amlodipine besylate was retained in oral liquid composition #7 in the sealed container closure system over the course of the intermediate stability conditions assay for 3 months.

Table 18 reports the stability data for oral liquid compositions #5, #6, and #7, tested under accelerated conditions (40° C.±2° C. and NMT 25% RH) in the sealed container closure system, at for a 3 month time interval.

TABLE 18

Stability assay for oral liquid compositions #5, #6, and #7 tested under accelerated conditions (40° C. ± 2° C. and NMT 25% RH) and stored in container closure system.

| Time | Composition #5 (% amlodipine besylate) | Composition #6 (% amlodipine besylate) | Composition #7 (% amlodipine besylate) |
|---|---|---|---|
| Initial | 101.2 | 97.6 | 99.5 |
| 1 month | 99.8 | 96.1 | 90.6 |
| 3 months | 92.7 | 90.6 | 84.2 |

As indicated in Table 18, oral liquid composition #5 was stable for at least 3 months when stored under accelerated conditions (40° C.±2° C. and NMT 25% RH) in the sealed container closure system. The stability assay showed that 92.7% of the original amlodipine besylate was retained in the oral liquid composition #5 in the sealed container closure system over the course of the accelerated stability conditions assay for 3 months. The stability assay also showed that 90.6% of the original amlodipine besylate was retained in oral liquid composition #6 in the sealed container closure system over the course of the intermediate stability conditions assay for 3 months.

Table 19 reports the stability data for oral liquid compositions #5, #6, and #7, stored under refrigerated conditions (5° C.±3° C.), standard conditions (25° C.±2° C., 60%±5% RH), intermediate conditions (35° C.±2° C., 65%±5% RH), or accelerated conditions (40° C.±2° C., NMT 25% RH) and in the sealed container closure system, for a 6 month or a 9 month time interval.

TABLE 19

Stability assay for oral liquid compositions #5, #6, and #7 tested under various conditions and stored in container closure system for 6 or 9 months.

| Time | Conditions | Composition #5 (% amlodipine besylate) | Composition #6 (% amlodipine besylate) | Composition #7 (% amlodipine besylate) |
|---|---|---|---|---|
| Initial | — | 101.2 | 97.6 | 99.5 |
| 6 months | Accelerated | 82.0 | 84.2 | 78.9 |
| 6 months | Intermediate | 95.0 | 95.0 | 83.3 |
| 6 months | Standard | 97.4 | 97.8 | 94.6 |
| 6 months | Refrigerated | NE* | 98.7 | 99.5 |
| 9 months | Intermediate | 94.3 | NE | NE |
| 9 months | Standard | 96.6 | NE | NE |

*Not evaluated

As indicated in Table 15, oral liquid composition #6 and #7 was stable for at least 6 months when stored under intermediate or standard conditions in the container closure system. It follows that composition #6 also would be stable for at least 6 months if stored under refrigerated conditions in the container closure system. Composition #5 also was stable for at least 9 months when stored in the container closure system under standard and intermediate conditions. Composition #6 was observed to be stable for at least 6 months when stored under any of intermediate, standard, and refrigerated conditions in the container closure system, but was not evaluated for stability at 9 months under those conditions. Composition #7 was observed to be stable for at least 6 months when stored under standard or refrigerated conditions in the container closure system. Composition #7 was not evaluated for stability at 9 months.

The following numbered clauses are directed to various non-limiting examples of inventions according to the present disclosure:

1. An oral liquid pharmaceutical composition comprising:
    about 0.1 to about 1.9 mg/mL amlodipine besylate;
    about 5 mg/mL to about 90 mg/mL cyclodextrin;
    about 0.5 mg/mL to about 4 mg/mL paraben; and
    water.
2. The oral liquid pharmaceutical composition of clause 1, comprising about 0.6 mg/mL to about 1.4 mg/mL amlodipine besylate.
3. The oral liquid pharmaceutical composition of any of clauses 1 and 2, comprising about 0.8 mg/mL to about 1.2 mg/mL amlodipine besylate.

4. The oral liquid pharmaceutical composition of any of clauses 1-3, comprising about 1 mg/mL amlodipine besylate.
5. The oral liquid pharmaceutical composition of any of clauses 1-4, comprising about 30 mg/mL to about 70 mg/mL cyclodextrin.
6. The oral liquid pharmaceutical composition of any of clauses 1-5, comprising about 10 mg/mL to about 60 mg/mL cyclodextrin.
7. The oral liquid pharmaceutical composition of any of clauses 1-6, comprising about 50 mg/mL cyclodextrin.
8. The oral liquid pharmaceutical composition of any of clauses 1-7, wherein the cyclodextrin comprises one or more of α-cyclodextrin, β-cyclodextrin, and γ-cyclodextrin.
9. The oral liquid pharmaceutical composition of any of clauses 1-8, wherein the cyclodextrin comprises hydroxypropyl β-cyclodextrin.
10. The oral liquid pharmaceutical composition of any of clauses 1-9, comprising about 5 mg/mL to about 90 mg/mL β-cyclodextrin.
11. The oral liquid pharmaceutical composition of any of clauses 1-10, comprising about 50 mg/mL β-cyclodextrin.
12. The oral liquid pharmaceutical composition of any of clauses 1-11, comprising about 5 mg/mL to about 90 mg/mL hydroxypropyl β-cyclodextrin.
13. The oral liquid pharmaceutical composition of any of clauses 1-12, comprising about 50 mg/mL hydroxypropyl β-cyclodextrin.
14. The oral liquid pharmaceutical composition of any of clauses 1-13, comprising about 0.5 mg/mL to about 4 mg/mL paraben.
15. The oral liquid pharmaceutical composition of any of clauses 1-14, comprising about 1.2 mg/mL to about 2.8 mg/mL paraben.
16. The oral liquid pharmaceutical composition of any of clauses 1-15, comprising about 1.5 mg/mL to about 2.5 mg/mL paraben.
17. The oral liquid pharmaceutical composition of any of clauses 1-16, comprising about 2 mg/mL paraben.
18. The oral liquid pharmaceutical composition of any of clauses 1-17, further comprising about 0.02 mg/mL to about 0.12 mg/mL curcumin.
19. The oral liquid pharmaceutical composition of any of clauses 1-18, further comprising about 0.04 mg/mL to about 0.10 mg/mL curcumin.
20. The oral liquid pharmaceutical composition of any of clauses 1-19, further comprising about 0.06 mg/mL to about 0.08 mg/mL curcumin.
21. The oral liquid pharmaceutical composition of any of clauses 1-20, wherein the paraben comprises one or more of methylparaben, ethylparaben, propylparaben, and butylparaben.
22. The oral liquid pharmaceutical composition of any of clauses 1-21, wherein a mole ratio of cyclodextrin to amlodipine besylate is about 5:1 to about 75:1.
23. The oral liquid pharmaceutical composition of any of clauses 1-22, wherein the composition comprises curcumin and a mole ratio of curcumin to amlodipine besylate is about 150:1 to about 250:1.
24. The oral liquid pharmaceutical composition of any of clauses 1-23, further comprising one or more of a sweetener, a flavoring agent, a stabilizer, a coloring agent, and a thickener.
26. An oral liquid pharmaceutical composition comprising:
about 0.8 to about 1.2 mg/mL amlodipine besylate; about 10 mg/mL to about 60 mg/mL cyclodextrin; about 1.5 mg/mL to about 2.5 mg/mL paraben; and water.
27. The oral liquid pharmaceutical composition of clause 26, wherein the cyclodextrin comprises one or more of α-cyclodextrin, β-cyclodextrin, and γ-cyclodextrin.
28. The oral liquid pharmaceutical composition of any of clauses 26 and 27, wherein the cyclodextrin comprises hydroxypropyl β-cyclodextrin.
29. The oral liquid pharmaceutical composition of any of clauses 26-28, wherein the paraben comprises one or more of methylparaben, ethylparaben, propylparaben, and butylparaben.
30. The oral liquid pharmaceutical composition of any of clauses 26-29, wherein a mole ratio of cyclodextrin to amlodipine besylate is about 5:1 to about 75:1.
31. The oral liquid pharmaceutical composition of any of clauses 26-30, wherein the composition comprises curcumin and a mole ratio of curcumin to amlodipine besylate is about 150:1 to about 250:1.
32. The oral liquid pharmaceutical composition of any of clauses 26-31, further comprising one or more of a sweetener, a flavoring agent, a stabilizer, a coloring agent, and a thickener.
33. The oral liquid pharmaceutical composition of any of clauses 1-32, provided that a volume of the oral liquid pharmaceutical composition retains at least 90% of an initial concentration of amlodipine besylate after the volume has been stored in a sealed container for three months at 2° C. to 8° C.
34. The oral liquid pharmaceutical composition of any of clauses 1-32, provided that a volume of the oral liquid pharmaceutical composition retains at least 90% of an initial concentration of amlodipine besylate after the volume has been stored in a sealed container for six months at 2° C. to 8° C.
35. The oral liquid pharmaceutical composition of any of clauses 1-32, provided that a volume of the oral liquid pharmaceutical composition retains at least 95% of an initial concentration of amlodipine besylate after the volume has been stored in a sealed container for three months at 2° C. to 8° C.
36. The oral liquid pharmaceutical composition of any of clauses 1-32, provided that a volume of the oral liquid pharmaceutical composition retains at least 95% of an initial concentration of amlodipine besylate after the volume has been stored in a sealed container for six months at 2° C. to 8° C.
37. The oral liquid pharmaceutical composition of any of clauses 1-36, provided that a volume of the oral liquid pharmaceutical composition retains at least 90% of an initial concentration of amlodipine besylate after the volume has been stored in a sealed container for three months at 23° C. to 27° C. and 55% to 65% relative humidity.
38. The oral liquid pharmaceutical composition of any of clauses 1-36, provided that a volume of the oral liquid pharmaceutical composition retains at least 90% of an initial concentration of amlodipine besylate after the volume has been stored in a sealed container for six months at 23° C. to 27° C. and 55% to 65% relative humidity.
39. The oral liquid pharmaceutical composition of any of clauses 1-36, provided that a volume of the oral liquid pharmaceutical composition retains at least 95% of an initial concentration of amlodipine besylate after the volume has been stored in a sealed container for three months at 23° C. to 27° C. and 55% to 65% relative humidity.

40. The oral liquid pharmaceutical composition of any of clauses 1-36, provided that a volume of the oral liquid pharmaceutical composition retains at least 95% of an initial concentration of amlodipine besylate after the volume has been stored in a sealed container for six months at 23° C. to 27° C. and 55% to 65% relative humidity.

41. The oral liquid pharmaceutical composition of any of clauses 1-40, provided that a volume of the oral liquid pharmaceutical composition retains at least 90% of an initial concentration of amlodipine besylate after the volume has been stored in a sealed container for three months at 28° C. to 32° C. and 60% to 70% relative humidity.

42. The oral liquid pharmaceutical composition of any of clauses 1-40, provided that a volume of the oral liquid pharmaceutical composition retains at least 90% of an initial concentration of amlodipine besylate after the volume has been stored in a sealed container for six months at 28° C. to 32° C. and 60% to 70% relative humidity.

43. The oral liquid pharmaceutical composition of any of clauses 1-40, provided that a volume of the oral liquid pharmaceutical composition retains at least 95% of an initial concentration of amlodipine besylate after the volume has been stored in a sealed container for three months at 28° C. to 32° C. and 60% to 70% relative humidity.

44. The oral liquid pharmaceutical composition of any of clauses 1-40, provided that a volume of the oral liquid pharmaceutical composition retains at least 95% of an initial concentration of amlodipine besylate after the volume has been stored in a sealed container for six months at 28° C. to 32° C. and 60% to 70% relative humidity.

45. The oral liquid pharmaceutical composition of any of clauses 1-44, provided that a volume of the oral liquid pharmaceutical composition retains at least 90% of an initial concentration of amlodipine besylate after the volume has been stored in a sealed container for one month at 38° C. to 42° C. and not greater than 25% relative humidity 46. The oral liquid pharmaceutical composition of any of clauses 1-44, provided that a volume of the oral liquid pharmaceutical composition retains at least 90% of an initial concentration of amlodipine besylate after the volume has been stored in a sealed container for three months at 38° C. to 42° C. and not greater than 25% relative humidity.

47. The oral liquid pharmaceutical composition of any of clauses 1-44, provided that a volume of the oral liquid pharmaceutical composition retains at least 95% of an initial concentration of amlodipine besylate after the volume has been stored in a sealed container for three months at 38° C. to 42° C. and not greater than 25% relative humidity.

48. The oral liquid pharmaceutical composition of any of clauses 1-47, provided that a volume of the oral liquid pharmaceutical composition retains at least 90% of an initial concentration of amlodipine besylate after the volume has been stored in a sealed container for nine months at 23° C. to 27° C. and 55% to 65% relative humidity.

49. The oral liquid pharmaceutical composition of any of clauses 1-48, provided that a volume of the oral liquid pharmaceutical composition retains at least 90% of an initial concentration of amlodipine besylate after the volume has been stored in a sealed container for nine months at 28° C. to 32° C. and 60% to 70% relative humidity.

50. A method of treating hypertension, the method comprising administering to a subject in need thereof a therapeutically effective amount of the oral liquid pharmaceutical composition of any of clauses 1-49.

51. A method of treating heart failure, the method comprising administering to a subject in need thereof a therapeutically effective amount of the oral liquid pharmaceutical composition of any of clauses 1-49.

52. A method of treating coronary artery disease, the method comprising administering to a subject in need thereof a therapeutically effective amount of the oral liquid pharmaceutical composition of any of clauses 1-49.

It will be understood that the present description illustrates those aspects of the invention relevant to a clear understanding of the invention. Certain aspects that would be apparent to those of ordinary skill in the art and that, therefore, would not facilitate a better understanding of the invention have not been presented in order to simplify the present description. Although only a limited number of embodiments of the present invention are necessarily described herein, one of ordinary skill in the art will, upon considering the foregoing description, recognize that many modifications and variations of the invention may be employed. All such variations and modifications of the invention are intended to be covered by the foregoing description and the following claims.

What is claimed is:

1. An oral liquid pharmaceutical composition consisting of:
   about 0.1 to about 1.9 mg/mL amlodipine besylate;
   about 5 mg/mL to about 90 mg/mL cyclodextrin;
   about 0.5 mg/mL to about 4 mg/mL paraben;
   optionally, at least one additional preservative;
   optionally, at least one sweetener;
   optionally, at least one flavoring agent;
   optionally, at least one coloring agent; and
   water.

2. The oral liquid pharmaceutical composition of claim 1, wherein a concentration of amlodipine besylate is about 0.8 mg/mL to about 1.2 mg/mL.

3. The oral liquid pharmaceutical composition of claim 1, wherein a concentration of amlodipine besylate is about 1 mg/mL.

4. The oral liquid pharmaceutical composition of claim 1, wherein a concentration of cyclodextrin is about 10 mg/mL to about 60 mg/mL.

5. The oral liquid pharmaceutical composition of claim 1, wherein a concentration of cyclodextrin is about 50 mg/mL.

6. The oral liquid pharmaceutical composition of claim 1, wherein the cyclodextrin comprises β-cyclodextrin in a concentration of about 5 mg/mL to about 90 mg/mL based on total volume of the oral liquid pharmaceutical composition.

7. The oral liquid pharmaceutical composition of claim 1, wherein the cyclodextrin comprises β-cyclodextrin in a concentration of about 50 mg/mL based on total volume of the oral liquid pharmaceutical composition.

8. The oral liquid pharmaceutical composition of claim 1, wherein a concentration of paraben is about 0.5 mg/mL to about 4 mg/mL.

9. The oral liquid pharmaceutical composition of claim 1, wherein a concentration of paraben is about 1.5 mg/mL to about 2.5 mg/mL.

10. The oral liquid pharmaceutical composition of claim 1, wherein a concentration of paraben is about 2 mg/mL.

11. The oral liquid pharmaceutical composition of claim 1, wherein a mole ratio of cyclodextrin to amlodipine besylate is about 5:1 to about 75:1.

12. The oral liquid pharmaceutical composition of claim 1, provided that a volume of the oral liquid pharmaceutical composition retains at least 90% of an initial concentration of amlodipine besylate after the volume has been stored in a sealed container for three months at 2° C. to 8° C.

13. The oral liquid pharmaceutical composition of claim 1, provided that a volume of the oral liquid pharmaceutical composition retains at least 90% of an initial concentration of amlodipine besylate after the volume has been stored in a sealed container for three months at 23° C. to 27° C. and 55% to 65% relative humidity.

14. The oral liquid pharmaceutical composition of claim 1, provided that a volume of the oral liquid pharmaceutical composition retains at least 90% of an initial concentration of amlodipine besylate after the volume has been stored in a sealed container for six months at 23° C. to 27° C. and 55% to 65% relative humidity.

15. The oral liquid pharmaceutical composition of claim 1, provided that a volume of the oral liquid pharmaceutical composition retains at least 90% of an initial concentration of amlodipine besylate after the volume has been stored in a sealed container for three months at 28° C. to 32° C. and 60% to 70% relative humidity.

16. The oral liquid pharmaceutical composition of claim 1, provided that a volume of the oral liquid pharmaceutical composition retains at least 90% of an initial concentration of amlodipine besylate after the volume has been stored in a sealed container for one month at 38° C. to 42° C. and not greater than 25% relative humidity.

17. An oral liquid pharmaceutical composition consisting of:
about 0.8 to about 1.2 mg/mL amlodipine besylate;
about 10 mg/mL to about 60 mg/mL cyclodextrin;
about 1.5 mg/mL to about 2.5 mg/mL paraben;
optionally, at least one additional preservative;
optionally, at least one sweetener;
optionally, at least one flavoring agent;
optionally, at least one coloring agent; and
water;
provided that a volume of the oral liquid pharmaceutical composition retains at least 90% of an initial concentration of amlodipine besylate after the volume has been stored in a sealed container for three months at 23° C. to 27° C. and 55% to 65% relative humidity.

18. The oral liquid composition of claim 17, wherein the cyclodextrin comprises β-cyclodextrin.

19. The oral liquid pharmaceutical composition of claim 17, wherein the cyclodextrin comprises hydroxypropyl β-cyclodextrin.

20. The oral liquid pharmaceutical composition of claim 17, wherein a mole ratio of cyclodextrin to amlodipine besylate is about 5:1 to about 75:1.

21. The oral liquid pharmaceutical composition of claim 17, provided that a volume of the oral liquid pharmaceutical composition retains at least 90% of an initial concentration of amlodipine besylate after the volume has been stored in a sealed container for one month at 38° C. to 42° C. and not greater than 25% relative humidity.

22. The oral liquid pharmaceutical composition of claim 17, wherein a concentration of amlodipine besylate is about 1 mg/mL.

23. A method of treating a condition selected from hypertension, heart failure, and coronary artery disease, the method comprising administering to a subject in need thereof a therapeutically effective amount of the oral liquid pharmaceutical composition of claim 1.

24. A method of a condition selected from hypertension, heart failure, and coronary artery disease, the method comprising administering to a subject in need thereof a therapeutically effective amount of the oral liquid pharmaceutical composition of claim 17.

* * * * *